(12) United States Patent
Carr et al.

(10) Patent No.: US 7,615,615 B2
(45) Date of Patent: Nov. 10, 2009

(54) MODIFIED INTERFERON BETA WITH REDUCED IMMUNOGENICITY

(75) Inventors: Francis J. Carr, Balmedie (GB); Graham Carter, By Newmachar (GB); Tim Jones, Babraham (GB); John Watkins, Girton (GB); Matthew Baker, Littleport (GB)

(73) Assignee: Merck Patent GmbH, Darmstadt (DE)

( * ) Notice: Subject to any disclaimer, the term of this patent is extended or adjusted under 35 U.S.C. 154(b) by 38 days.

(21) Appl. No.: 12/077,120

(22) Filed: Mar. 17, 2008

(65) Prior Publication Data

US 2009/0043076 A1    Feb. 12, 2009

Related U.S. Application Data

(62) Division of application No. 10/471,894, filed as application No. PCT/EP02/02925 on Mar. 15, 2002, now Pat. No. 7,381,795.

(30) Foreign Application Priority Data

Mar. 15, 2001   (EP)   .................. 01106539

(51) Int. Cl.
   *C07K 14/00*   (2006.01)
   *A61K 38/19*   (2006.01)
   *C12N 15/24*   (2006.01)
(52) U.S. Cl. .................. 530/351; 530/350; 424/85.1; 435/69.1
(58) Field of Classification Search ............. None
   See application file for complete search history.

(56) References Cited

U.S. PATENT DOCUMENTS 6,514,729 B1 * 2/2003 Bentzien ............. 435/69.51
6,800,735 B2 * 10/2004 Whitty et al. ............ 530/351
7,381,795 B2 * 6/2008 Carr et al. .............. 530/351

* cited by examiner

*Primary Examiner*—Manjunath N Rao
*Assistant Examiner*—Jegatheesan Seharaseyon
(74) *Attorney, Agent, or Firm*—Olson & Cepuritis, Ltd.

(57) ABSTRACT

The present invention relates a modified human interferon beta (INFβ) which is less immunogenic than human INFβ (SEQ ID NO: 1) when administered in vivo to a human. The modified human INFβ comprises an amino acid residue sequence that differs from SEQ ID NO: 1 by an amino acid residue substitution selected from the group consisting of L57A, L57C, L57D L57E, L57G, L57H, L57K, L57N, L57P, L57Q, L57R, L57S, and L57T and an additional substitution selected from the group consisting of the H140A, H140C, H140G, and H140P.

7 Claims, 19 Drawing Sheets

FIGURE 1

Peptide sequences in human INFβ with potential human MHC class II binding activity.

```
MSYNLLGFLQRSS  (SEQ ID NO: 10),    YNLLGFLQRSSNF  (SEQ ID NO: 11),
NLLGFLQRSSNFQ  (SEQ ID NO: 12),    LLGFLQRSSNFQC  (SEQ ID NO: 13),
LGFLQRSSNFQCQ  (SEQ ID NO: 14),    GFLQRSSNFQCQK  (SEQ ID NO: 15),
RSSNFQCQKLLWQ  (SEQ ID NO: 16),    SNFQCQKLLWQLN  (SEQ ID NO: 17),
QKLLWQLNGRLEY  (SEQ ID NO: 18),    KLLWQLNGRLEYC  (SEQ ID NO: 19),
LLWQLNGRLEYCL  (SEQ ID NO: 20),    WQLNGRLEYCLKD  (SEQ ID NO: 21),
GRLEYCLKDRMNF  (SEQ ID NO: 22),    LEYCLKDRMNFDI  (SEQ ID NO: 23),
YCLKDRMNFDIPE  (SEQ ID NO: 24),    DRMNFDIPEEIKQ  (SEQ ID NO: 25),
MNFDIPEEIKQLQ  (SEQ ID NO: 26),    FDIPEEIKQLQQF  (SEQ ID NO: 27),
DIPEEIKQLQQFQ  (SEQ ID NO: 28),    EEIKQLQQFQKED  (SEQ ID NO: 29),
KQLQQFQKEDAAL  (SEQ ID NO: 30),    QLQQFQKEDAALT  (SEQ ID NO: 31),
QQFQKEDAALTIY  (SEQ ID NO: 32),    FQKEDAALTIYEM  (SEQ ID NO: 33),
KEDAALTIYEMLQ  (SEQ ID NO: 34),    AALTIYEMLQNIF  (SEQ ID NO: 35),
LTIYEMLQNIFAI  (SEQ ID NO: 36),    TIYEMLQNIFAIF  (SEQ ID NO: 37),
IYEMLQNIFAIFR  (SEQ ID NO: 38),    YEMLQNIFAIFRQ  (SEQ ID NO: 39),
EMLQNIFAIFRQD  (SEQ ID NO: 40),    QNIFAIFRQDSSS  (SEQ ID NO: 41),
NIFAIFRQDSSST  (SEQ ID NO: 42),    FAIFRQDSSSTGW  (SEQ ID NO: 43),
AIFRQDSSSTGWN  (SEQ ID NO: 44),    TGWNETIVENLLA  (SEQ ID NO: 45),
GWNETIVENLLAN  (SEQ ID NO: 46),    WNETIVENLLANV  (SEQ ID NO: 47),
ETIVENLLANVYH  (SEQ ID NO: 48),    TIVENLLANVYHQ  (SEQ ID NO: 49),
ENLLANVYHQINH  (SEQ ID NO: 50),    NLLANVYHQINHL  (SEQ ID NO: 51),
ANVYHQINHLKTV  (SEQ ID NO: 52),    NVYHQINHLKTVL  (SEQ ID NO: 53),
HQINHLKTVLEEK  (SEQ ID NO: 54),    NHLKTVLEEKLEK  (SEQ ID NO: 55),
KTVLEEKLEKEDF  (SEQ ID NO: 56),    TVLEEKLEKEDFT  (SEQ ID NO: 57),
VLEEKLEKEDFTR  (SEQ ID NO: 58),    EKLEKEDFTRGKL  (SEQ ID NO: 59),
KLEKEDFTRGKLM  (SEQ ID NO: 60),    LEKEDFTRGKLMS  (SEQ (D NO: 61),
EKEDFTRGKLMSS  (SEQ ID NO: 62),    EDFTRGKLMSSLH  (SEQ ID NO: 63),
TRGKLMSSLHLKR  (SEQ ID NO: 64),    GKLMSSLHLKRYY  (SEQ ID NO: 65),
KLMSSLHLKRYYG  (SEQ ID NO: 66),    LMSSLHLKRYYGR  (SEQ ID NO: 67),
SSLHLKRYYGRIL  (SEQ ID NO: 68),    LHLKRYYGRILHY  (SEQ ID NO: 69),
KRYYGRILHYLKA  (SEQ ID NO: 70),    RYYGRILHYLKAK  (SEQ ID NO: 71),
YYGRILHYLKAKE  (SEQ ID NO: 72),    GRILHYLKAKEYS  (SEQ ID NO: 73),
RILHYLKAKEYSH  (SEQ ID NO: 74),    LHYLKAKEYSHCA  (SEQ ID NO: 75),
HYLKAKEYSHCAW  (SEQ ID NO: 76),    YLKAKEYSHCAWT  (SEQ ID NO: 77),
KEYSHCAWTIVRV  (SEQ ID NO: 78),    HCAWTIVRVEILR  (SEQ ID NO: 79),
CAWTIVRVEILRN  (SEQ ID NO: 80),    WTIVRVEILRNFY  (SEQ ID NO: 81),
TIVRVEILRNFYF  (SEQ ID NO: 82),    IVRVEILRNFYFI  (SEQ ID NO: 83),
VRVEILRNFYFIN  (SEQ ID NO: 84),    VEILRNFYFINRL  (SEQ ID NO: 85),
EILRNFYFINRLT  (SEQ ID NO: 86),    LRNFYFINRLTGY  (SEQ ID NO: 87),
RNFYFINRLTGYL  (SEQ ID NO: 88),    NFYFINRLTGYLR  (SEQ ID NO: 89),
FYFINRLTGYLRN  (SEQ ID NO: 90)
```

FIGURE 2

| Residue # | WT Residue | Substitutions | | | | | | | | | | | | |
|---|---|---|---|---|---|---|---|---|---|---|---|---|---|
| 3 | Y | A | C | D | E | G | H | K | N | P | Q | R | S | T |
| 6 | L | N | P | Q | R | S | T | | | | | | | |
| 8 | F | A | C | D | E | G | H | K | N | P | Q | R | S | T |
| 9 | L | A | C | D | E | G | H | K | N | P | Q | R | S | T |
| 15 | F | A | C | D | E | G | H | K | N | P | Q | R | S | T |
| 20 | L | A | C | D | E | G | H | K | N | P | Q | R | S | T |
| 21 | L | A | C | D | E | G | H | K | N | P | Q | R | S | T |
| 22 | W | A | C | D | E | G | H | K | N | P | Q | R | S | T |
| 24 | L | A | C | D | E | G | H | K | N | P | Q | R | S | T |
| 28 | L | A | C | D | E | G | H | K | N | P | Q | R | S | T |
| 30 | Y | A | C | D | E | G | H | K | N | P | Q | R | S | T |
| 32 | L | A | C | D | E | G | H | K | N | P | Q | R | S | |
| 36 | M | A | C | D | E | G | H | K | N | P | Q | R | S | T |
| 38 | F | A | C | D | E | G | H | K | N | P | Q | R | S | T |
| 40 | I | A | C | D | E | G | H | K | N | P | Q | R | S | T |
| 44 | I | A | C | D | E | G | H | K | N | P | Q | R | S | T |
| 47 | L | A | C | D | E | G | H | K | N | P | Q | R | S | T |
| 50 | F | A | C | D | E | G | H | K | N | P | Q | R | S | T |
| 57 | L | A | C | D | E | G | H | K | N | P | Q | R | S | T |
| 60 | Y | A | C | D | E | G | H | K | N | P | Q | R | S | T |
| 62 | M | A | C | D | E | G | H | K | N | P | Q | R | S | T |
| 63 | L | A | C | D | E | G | H | K | N | P | Q | R | S | T |
| 66 | I | A | C | D | E | G | H | K | N | P | Q | R | S | T |
| 67 | F | A | C | D | E | G | H | K | N | P | Q | R | S | T |
| 69 | I | A | C | D | E | G | H | K | N | P | Q | R | S | T |
| 70 | F | A | C | D | E | G | H | K | N | P | Q | R | S | T |
| 79 | W | A | C | D | E | G | H | K | N | P | Q | R | S | T |
| 83 | I | A | C | D | E | G | H | K | N | P | Q | R | S | T |
| 84 | V | A | C | D | E | | | K | N | P | Q | R | S | T |
| 87 | L | A | C | D | E | G | H | K | N | P | Q | R | S | T |
| 88 | L | A | C | D | E | G | H | K | N | P | Q | R | S | T |
| 91 | V | A | C | D | E | G | H | K | N | P | Q | R | S | T |
| 92 | Y | A | C | D | E | G | H | K | N | P | Q | R | S | T |
| 95 | I | A | C | D | E | G | H | K | N | P | Q | R | S | T |
| 98 | L | A | C | D | E | G | H | K | N | P | Q | R | S | T |
| 101 | V | A | C | D | E | G | H | K | N | P | Q | R | S | T |
| 102 | L | A | C | D | E | G | H | K | N | P | Q | R | S | T |
| 106 | L | A | C | D | E | G | H | K | N | P | Q | R | S | T |
| 111 | F | A | C | D | E | G | H | K | N | P | Q | R | S | T |
| 116 | L | A | C | D | E | G | H | K | N | P | Q | R | S | T |
| 117 | M | A | C | D | E | G | H | K | N | P | Q | R | S | T |
| 120 | L | A | C | D | E | G | H | K | N | P | Q | R | S | T |
| 122 | L | A | C | D | E | G | H | K | N | P | Q | R | S | T |
| 125 | Y | A | C | D | E | G | H | K | N | P | Q | R | S | T |
| 126 | Y | A | C | D | E | G | H | K | N | P | Q | R | S | T |
| 129 | I | A | C | D | E | G | H | K | N | P | Q | R | S | T |

FIGURE 2 cont...

| Residue # | WT Residue | Substitutions | | | | | | | | | | | |
|---|---|---|---|---|---|---|---|---|---|---|---|---|---|
| 130 | L | A | C | D | E | G | H | K | N | P | Q | R | S | T |
| 132 | Y | A | C | D | E | G | H | K | N | P | Q | R | S | T |
| 133 | L | A | C | D | E | G | H | K | N | P | Q | R | S | T |
| 138 | Y | A | C | D | E | G | H | K | N | P | Q | R | S | T |
| 143 | W | A | C | D | E | G | H | K | N | P | Q | R | S | T |
| 145 | I | A | C | D | E | G | H | K | N | P | Q | R | S | T |
| 146 | V | A | C | D | E | G | H | K | N | P | Q | R | S | T |
| 148 | V | A | C | D | E | G | H | K | N | P | Q | R | S | T |
| 150 | I | A | C | D | E | G | H | K | N | P | Q | R | S | T |
| 151 | L | A | C | D | E | G | H | K | N | P | Q | R | S | T |
| 154 | F | A | C | D | E | G | H | K | N | P | Q | R | S | T |
| 155 | Y | A | C | D | E | G | H | K | N | P | Q | R | S | T |
| 156 | F | A | C | D | E | G | H | K | N | P | Q | R | S | T |

FIGURE 3

| Residue # | WT residue | Substitution | | | | | | | | | |
|---|---|---|---|---|---|---|---|---|---|---|---|
| 6 | L | A | C | D | E | F | G | H | I | K | V | W | Y |
| 9 | L | F | I | M | V | W | Y |
| 10 | Q | A | C | G | I | P |
| 11 | R | A | C | G | P |
| 12 | S | P | T |
| 13 | S | A | C | G | P |
| 14 | N | D | H | P |
| 15 | F | M | W | Y |
| 16 | Q | A | C | G | P |
| 17 | C | D | E | H | K | N | P | Q | R | S | T |
| 18 | Q | H | P | T |
| 19 | K | A | C | G |
| 20 | L | W | Y |
| 21 | L | M | W | Y |
| 23 | Q | H | P | T |
| 24 | L | F | I | M | V | W | Y |
| 25 | N | A | C | G | P |
| 26 | G | H | T |
| 28 | L | F | I | M | V | W | Y |
| 29 | E | A | C | G | H | P | W |
| 30 | Y | M |
| 31 | C | D | E | H | K | N | P | Q | R | S | T |
| 32 | L | F | I | M | V | W | Y |
| 33 | K | A | C | G | H | P | T |
| 34 | D | A | C | G | P | T |
| 35 | R | A | C | H | P | T |
| 36 | M | F | I | M | V | W | Y |
| 37 | N | A | C | G | H | P | W |
| 38 | F | I | M | V | W | Y |
| 39 | D | A | C | G | P |
| 42 | E | A | C | G | P |
| 43 | E | H | P |
| 44 | I | M | W |
| 45 | K | A | C | G | P |
| 46 | Q | P | T |
| 47 | L | M | W | Y |
| 48 | Q | A | C | G | P |
| 50 | F | M | W |
| 51 | Q | A | C | G | P |
| 52 | K | A | C | G | H | P | T |
| 53 | E | H | P | T |
| 54 | D | A | C | G | P |
| 55 | A | C | D | E | G | H | K | N | P | Q | R | S | T |
| 56 | A | D | E | G | H | K | N | P | Q | R | S | T |
| 57 | L | M | V | W | Y |
| 58 | T | A | C | G | P |
| 61 | E | A | C | G | P |

FIGURE 3, first continuation...

| Residue # | WT residue | Substitution | | | | | | | | |
|---|---|---|---|---|---|---|---|---|---|---|
| 62 | M | W | Y | | | | | | | |
| 63 | L | F | M | V | W | Y | | | | |
| 64 | Q | A | C | G | P | | | | | |
| 65 | N | H | P | T | | | | | | |
| 66 | I | M | W | Y | | | | | | |
| 67 | F | M | W | Y | | | | | | |
| 68 | A | D | E | F | H | K | N | P | Q | R | S | T |
| 69 | I | M | | | | | | | | |
| 70 | F | M | W | | | | | | | |
| 71 | R | A | C | G | P | | | | | |
| 72 | Q | A | C | G | P | T | | | | |
| 73 | D | A | C | G | P | T | | | | |
| 74 | S | A | C | G | P | T | | | | |
| 75 | S | P | T | | | | | | | |
| 76 | S | A | C | G | P | | | | | |
| 77 | T | A | C | G | P | | | | | |
| 78 | G | D | E | H | K | N | P | Q | R | S | T |
| 80 | N | A | C | G | P | | | | | |
| 81 | E | A | C | G | P | | | | | |
| 82 | T | P | | | | | | | | |
| 84 | V | L | M | W | Y | | | | | |
| 85 | E | P | T | | | | | | | |
| 86 | N | A | C | G | P | | | | | |
| 87 | L | F | I | M | V | W | Y | | | |
| 89 | A | H | P | | | | | | | |
| 90 | N | T | | | | | | | | |
| 100 | T | H | | | | | | | | |
| 102 | L | I | M | V | W | Y | | | | |
| 103 | E | A | C | G | P | T | | | | |
| 104 | E | P | | | | | | | | |
| 105 | K | H | Q | S | T | | | | | |
| 106 | L | M | W | Y | | | | | | |
| 107 | E | H | | | | | | | | |
| 108 | K | H | N | Q | S | T | | | | |
| 109 | E | P | T | | | | | | | |
| 110 | D | H | Q | S | T | | | | | |
| 111 | F | M | W | Y | | | | | | |
| 112 | T | A | C | G | P | | | | | |
| 114 | G | H | K | N | P | Q | S | T | | |
| 116 | L | F | I | M | V | W | Y | | | |
| 118 | S | A | C | G | P | | | | | |
| 119 | S | P | T | | | | | | | |
| 120 | L | M | W | Y | | | | | | |
| 121 | H | | | | | | | | | |
| 122 | L | W | Y | | | | | | | |
| 123 | K | A | C | G | P | T | | | | |
| 124 | R | A | C | G | P | T | | | | |

FIGURE 3, second continuation...

| Residue # | WT residue | Substitution | | | | | | | | | | | | |
|---|---|---|---|---|---|---|---|---|---|---|---|---|---|---|
| 127 | G | P | | | | | | | | | | | | |
| 128 | R | H | P | T | | | | | | | | | | |
| 129 | I | W | Y | | | | | | | | | | | |
| 130 | L | W | Y | | | | | | | | | | | |
| 133 | L | I | M | V | W | Y | | | | | | | | |
| 134 | K | A | C | G | H | P | | | | | | | | |
| 135 | A | C | G | H | K | N | P | Q | R | S | T | | | |
| 136 | K | P | T | | | | | | | | | | | |
| 137 | E | A | C | G | P | T | | | | | | | | |
| 139 | S | P | T | | | | | | | | | | | |
| 140 | H | A | C | G | P | | | | | | | | | |
| 141 | C | D | E | H | K | N | P | Q | R | S | T | | | |
| 145 | I | W | | | | | | | | | | | | |
| 148 | V | I | L | W | Y | | | | | | | | | |
| 151 | L | F | M | V | W | Y | | | | | | | | |
| 152 | R | A | C | G | P | W | Y | | | | | | | |
| 153 | N | A | C | G | P | T | | | | | | | | |
| 154 | F | M | | | | | | | | | | | | |
| 156 | F | I | M | W | Y | | | | | | | | | |
| 157 | I | T | | | | | | | | | | | | |
| 158 | N | A | C | F | G | I | L | M | P | V | W | Y | | |
| 159 | R | D | F | H | I | K | N | P | Q | S | T | V | W | Y |
| 160 | L | D | E | F | G | H | I | K | N | P | Q | R | S | T | Y |
| 161 | T | D | E | F | H | I | L | N | P | Q | S | V | W | Y |
| 162 | G | D | E | F | H | I | K | N | P | Q | R | S | T | V | W | Y |
| 164 | L | A | C | D | E | F | G | H | I | K | M | N | P | Q | R | S | T | V | W | Y |

FIGURE 4

| Substitution | | | Epitope Region |
|---|---|---|---|
| WT | # | MUT | |
| Leu | 57 | Ala | R1 |
| Tyr | 60 | Asn | R1 |
| Met | 62 | Ala | R1 |
| Leu | 63 | Ala | R1 |
| Ile | 66 | Thr | R1 |
| Phe | 67 | His | R1 |
| Ile | 69 | Ala | R1 |
| Ile | 59 | Ala | R1 |
| Phe | 50 | Ala | R1 |
| Phe | 70 | Ala | R1 |
| Tyr | 125 | Ala | R2 |
| Tyr | 126 | Ala | R2 |
| Ile | 129 | Ala | R2 |
| Leu | 130 | Ala | R2 |
| Tyr | 132 | Ser | R2 |
| Leu | 133 | Ala | R2 |
| Tyr | 138 | His | R2 |
| Tyr | 138 | Ala | R2 |

FIGURE 5

| ID # (SEQ#) | IFNβ-1a; 15mer sequence | Position of 1st peptide residue within IFNß-1a sequence | ID # (SEQ#) | IFNβ 1a; 15mer sequence | Position of 1st peptide residue within IFNß 1a sequence |
|---|---|---|---|---|---|
| 1 (91) | MSYNLLGFLQRSSNF | 1 | 28 (118) | TIVENLLANVYHQIN | 82 |
| 2 (92) | NLLGFLQRSSNFQCQ | 4 | 29 (119) | ENLLANVYHQINHLK | 85 |
| 3 (93) | GFLQRSSNFQCQKLL | 7 | 30 (120) | LANVYHQINHLKTVL | 88 |
| 4 (94) | QRSSNFQCQKLLWQL | 10 | 31 (121) | VYHQINHLKTVLEEK | 91 |
| 5 (95) | SNFQCQKLLWQLNGR | 13 | 32 (122) | QINHLKTVLEEKLEK | 94 |
| 6 (96) | QCQKLLWQLNGRLEY | 16 | 33 (123) | HLKTVLEEKLEKEDF | 97 |
| 7 (97) | KLLWQLNGRLEYCLK | 19 | 34 (124) | TVLEEKLEKEDFTRG | 100 |
| 8 (98) | WQLNGRLEYCLKDRM | 22 | 35 (125) | EEKLEKEDFTRGKLM | 103 |
| 9 (99) | NGRLEYCLKDRMNFD | 25 | 36 (126) | LEKEDFTRGKLMSSL | 106 |
| 10 (100) | LEYCLKDRMNFDIPE | 28 | 37 (127) | EDFTRGKLMSSLHLK | 109 |
| 11 (101) | CLKDRMNFDIPEEIK | 31 | 38 (128) | TRGKLMSSLHLKRYY | 112 |
| 12 (102) | DRMNFDIPEEIKQLQ | 34 | 39 (129) | KLMSSLHLKRYYGRI | 115 |
| 13 (103) | NFDIPEEIKQLQQFQ | 37 | 40 (130) | SSLHLKRYYGRILHY | 118 |
| 14 (104) | IPEEIKQLQQFQKED | 40 | 41 (131) | HLKRYYGRILHYLKA | 121 |
| 15 (105) | EIKQLQQFQKEDAAL | 43 | 42 (132) | RYYGRILHYLKAKEY | 124 |
| 16 (106) | QLQQFQKEDAALTIY | 46 | 43 (133) | GRILHYLKAKEYSHC | 127 |
| 17 (107) | QFQKEDAALTIYEML | 49 | 44 (134) | LHYLKAKEYSHCAWT | 130 |
| 18 (108) | KEDAALTIYEMLQNI | 52 | 45 (135) | LKAKEYSHCAWTIVR | 133 |
| 19 (109) | AALTIYEMLQNIFAI | 55 | 46 (136) | KEYSHCAWTIVRVEI | 136 |
| 20 (110) | TIYEMLQNIFAIFRQ | 58 | 47 (137) | SHCAWTIVRVEILRN | 139 |
| 21 (111) | EMLQNIFAIFRQDSS | 61 | 48 (138) | AWTIVRVEILRNFYF | 142 |
| 22 (112) | QNIFAIFRQDSSSTG | 64 | 49 (139) | IVRVEILRNFYFINR | 145 |
| 23 (113) | FAIFRQDSSSTGWNE | 67 | 50 (140) | VEILRNFYFINRLTG | 148 |
| 24 (114) | FRQDSSSTGWNETIV | 70 | 51 (141) | LRNFYFINRLTGYLR | 151 |
| 25 (115) | DSSSTGWNETIVENL | 73 | | | |
| 26 (116) | STGWNETIVENLLAN | 76 | | | |
| 27 (117) | WNETIVENLLANVYH | 79 | | | |

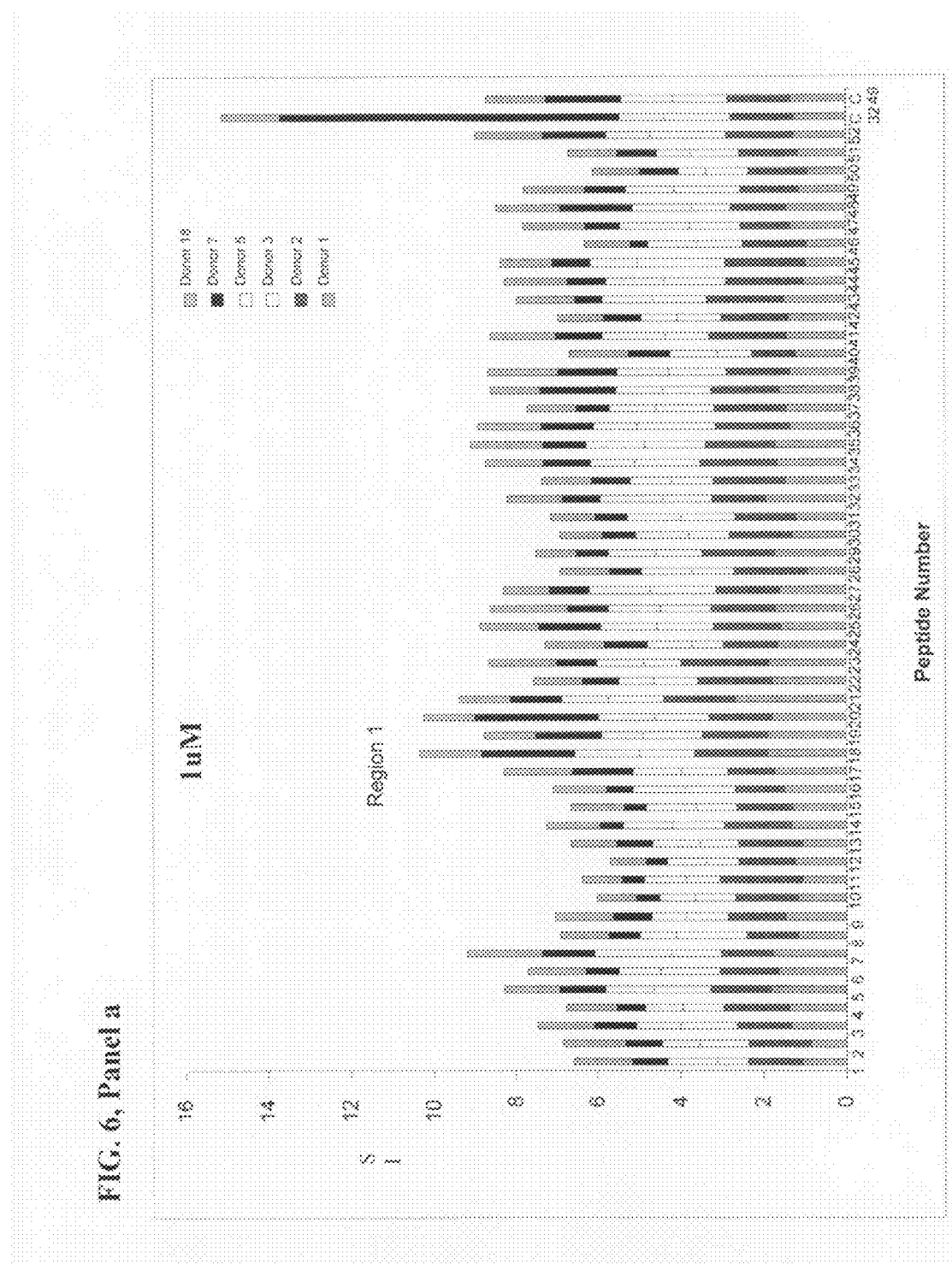
FIG. 6, Panel a

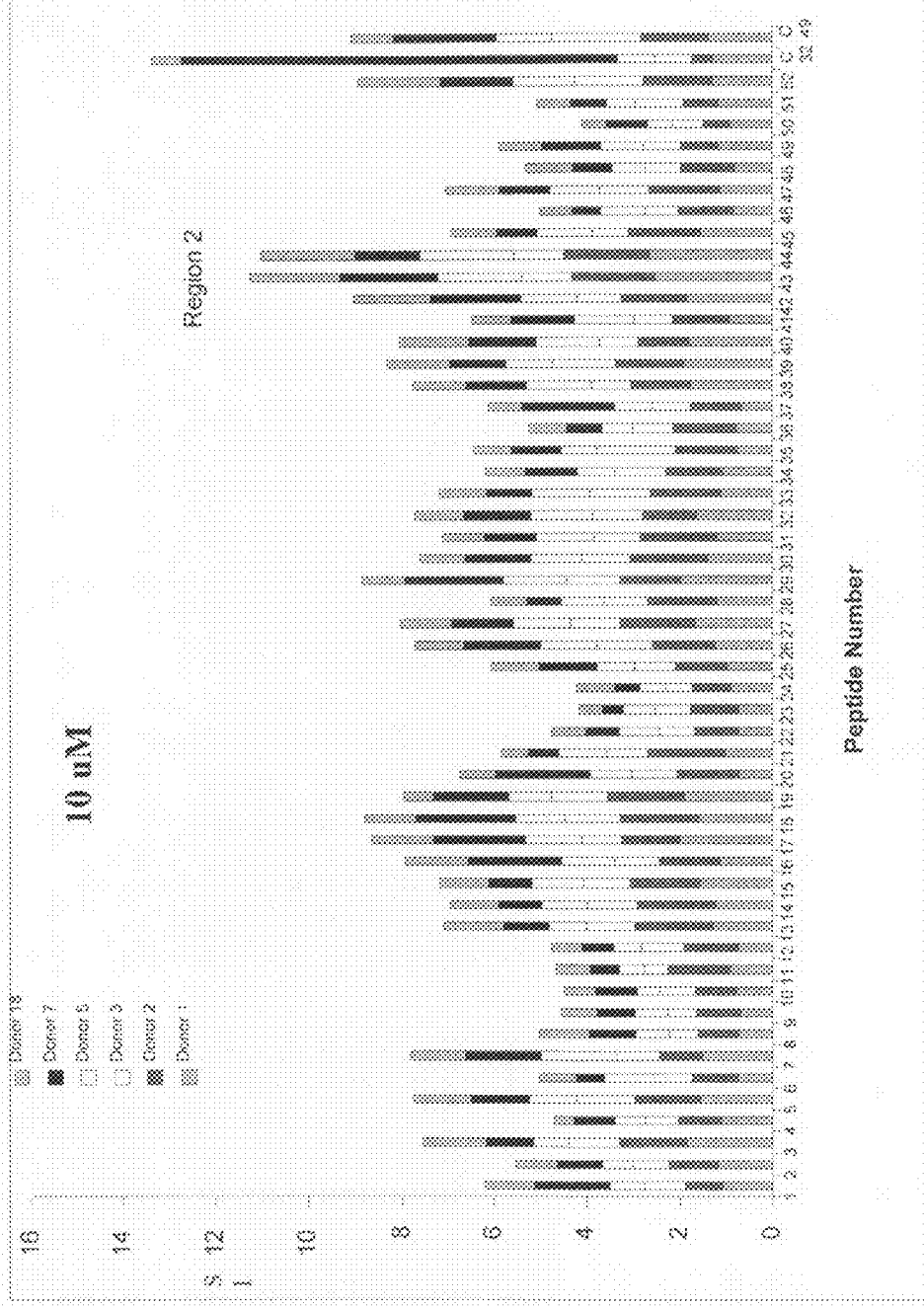

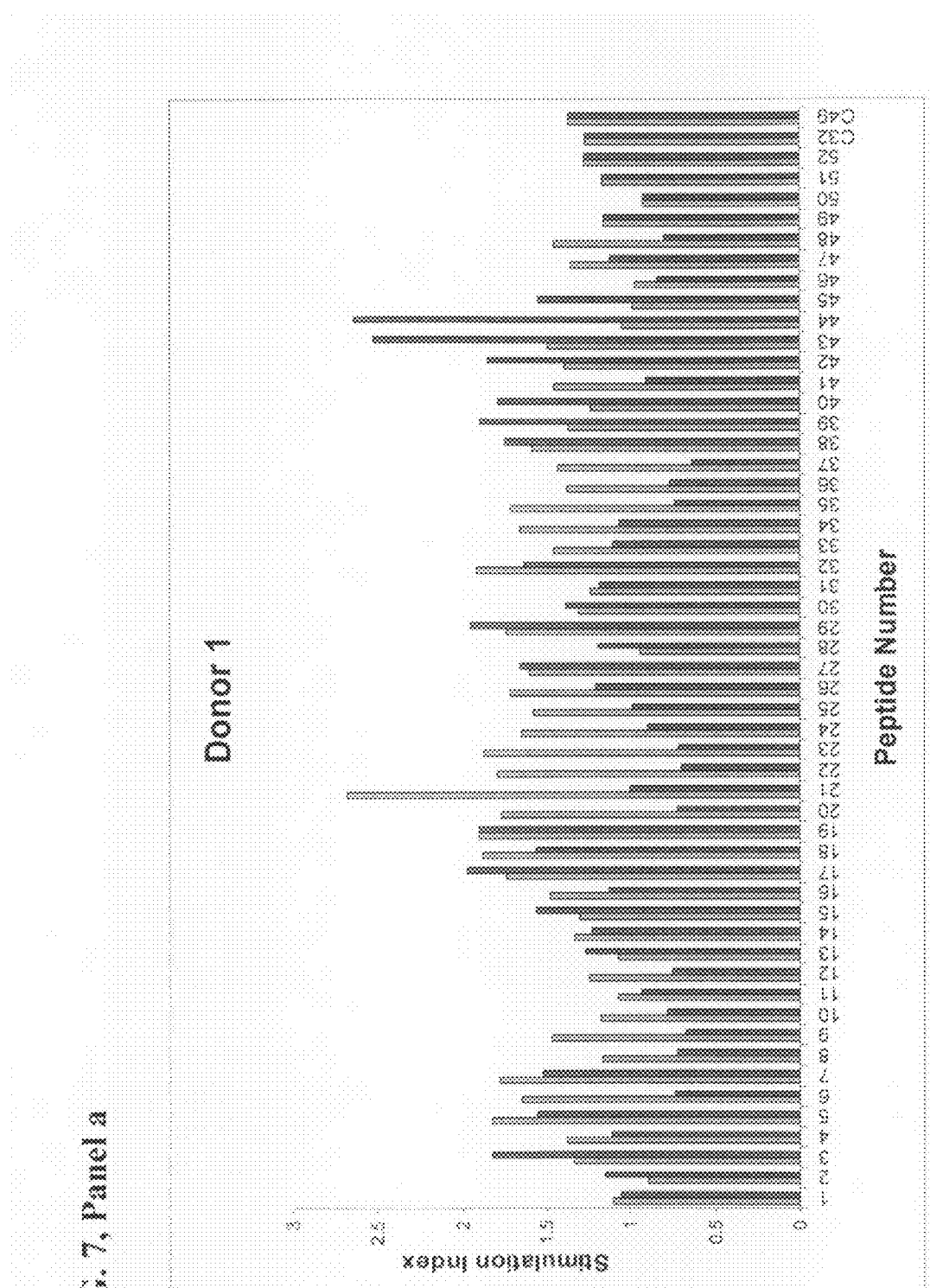
FIG. 7, Panel a

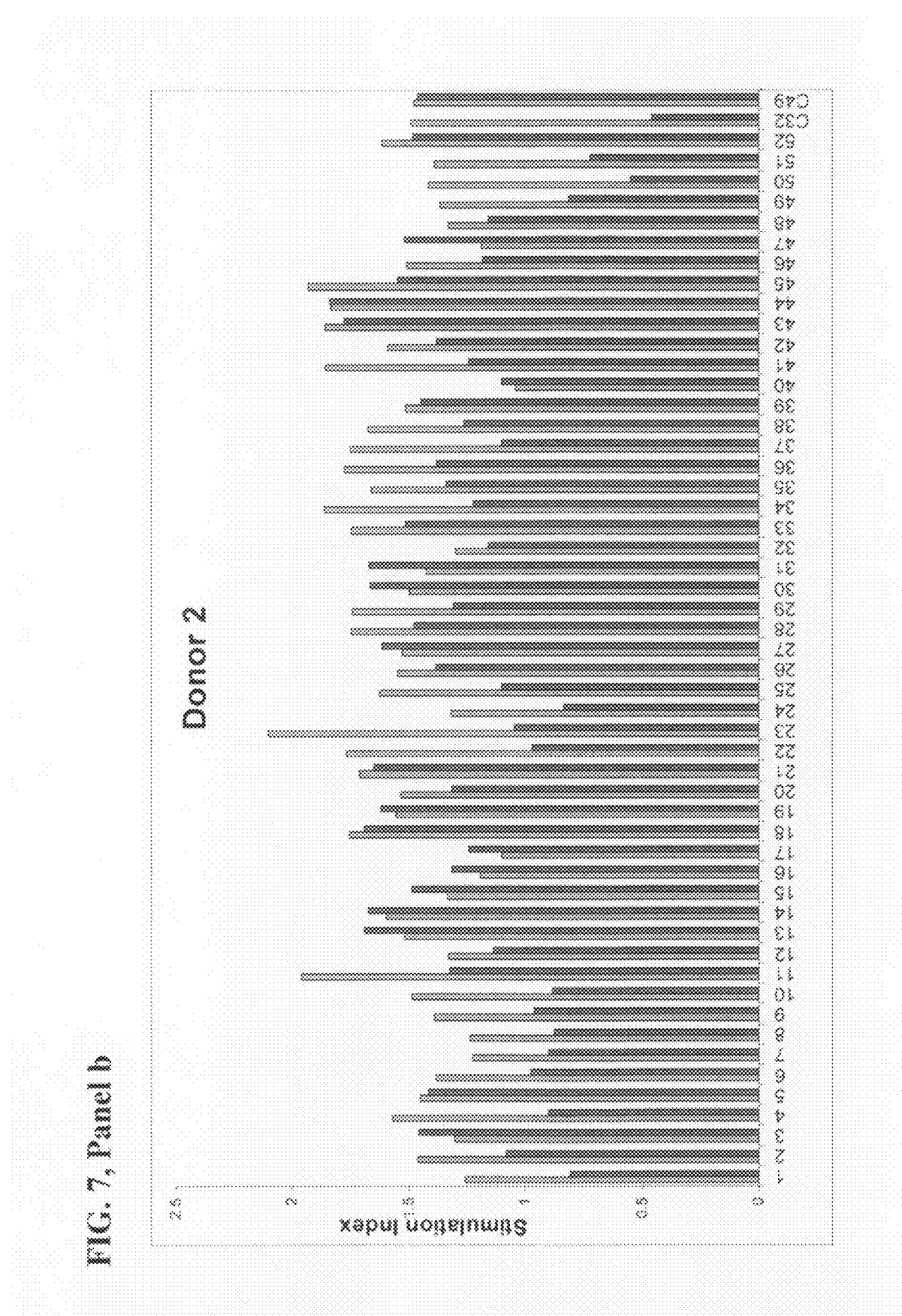
FIG. 7, Panel b

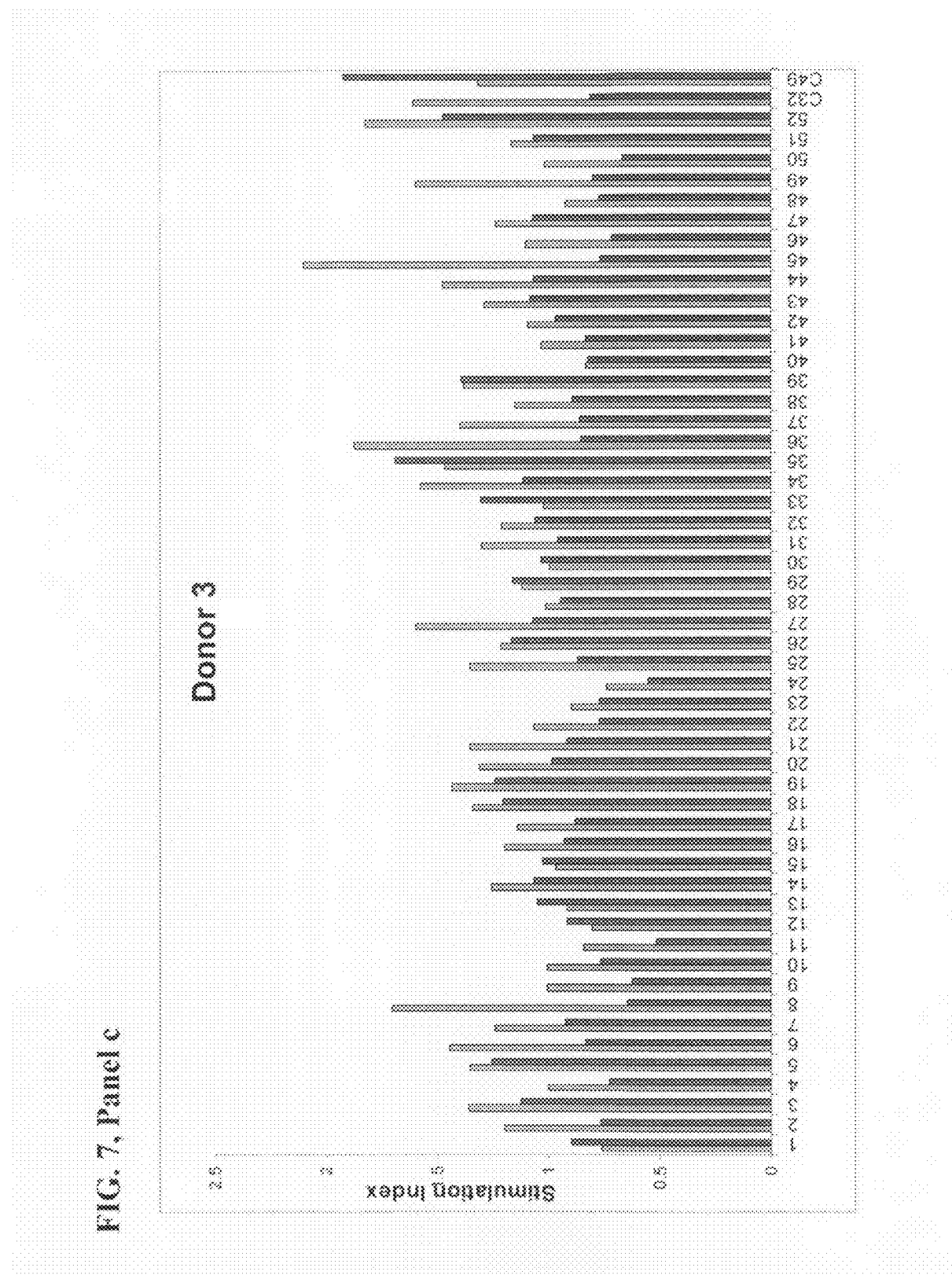
FIG. 7, Panel c

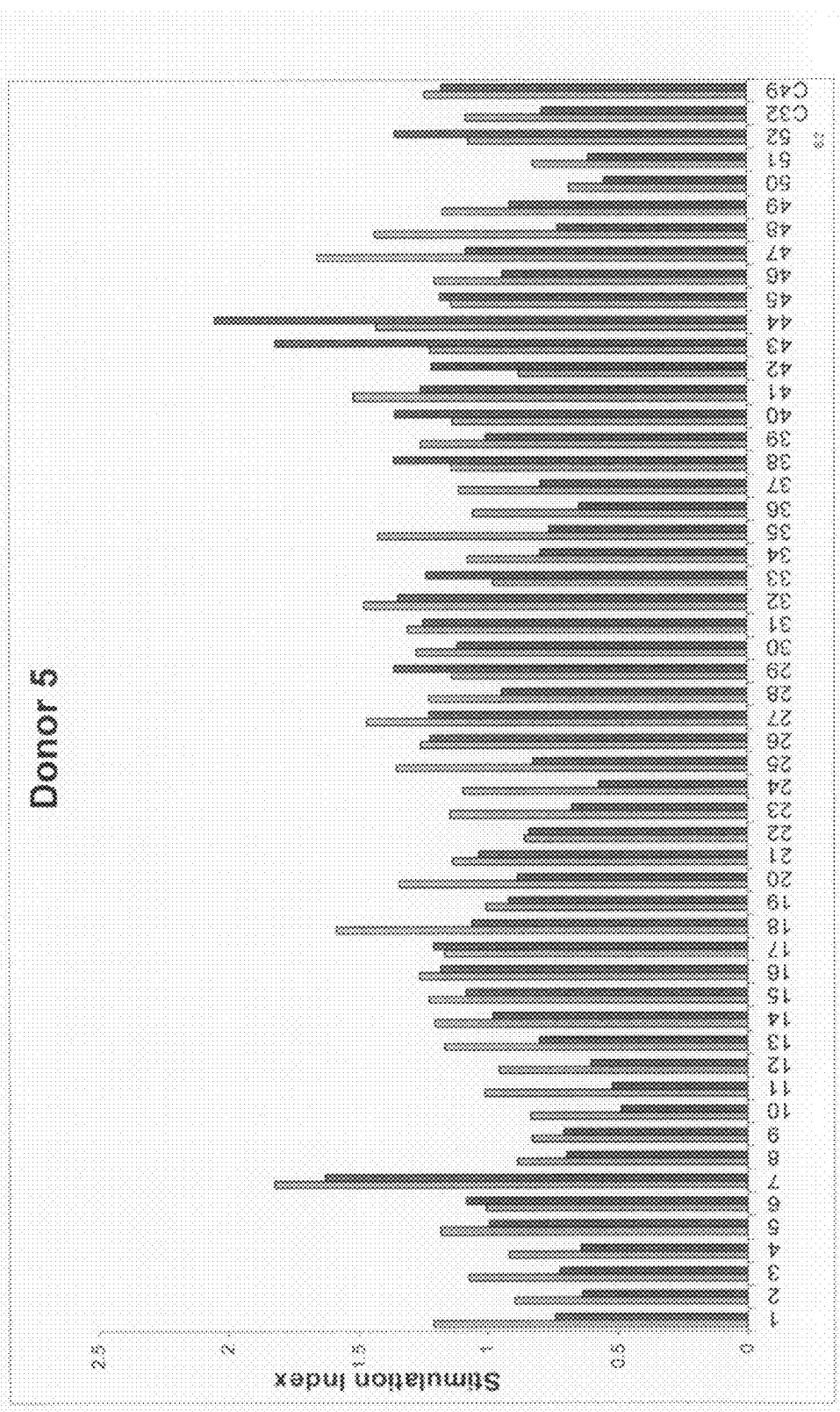
FIG. 7, Panel d

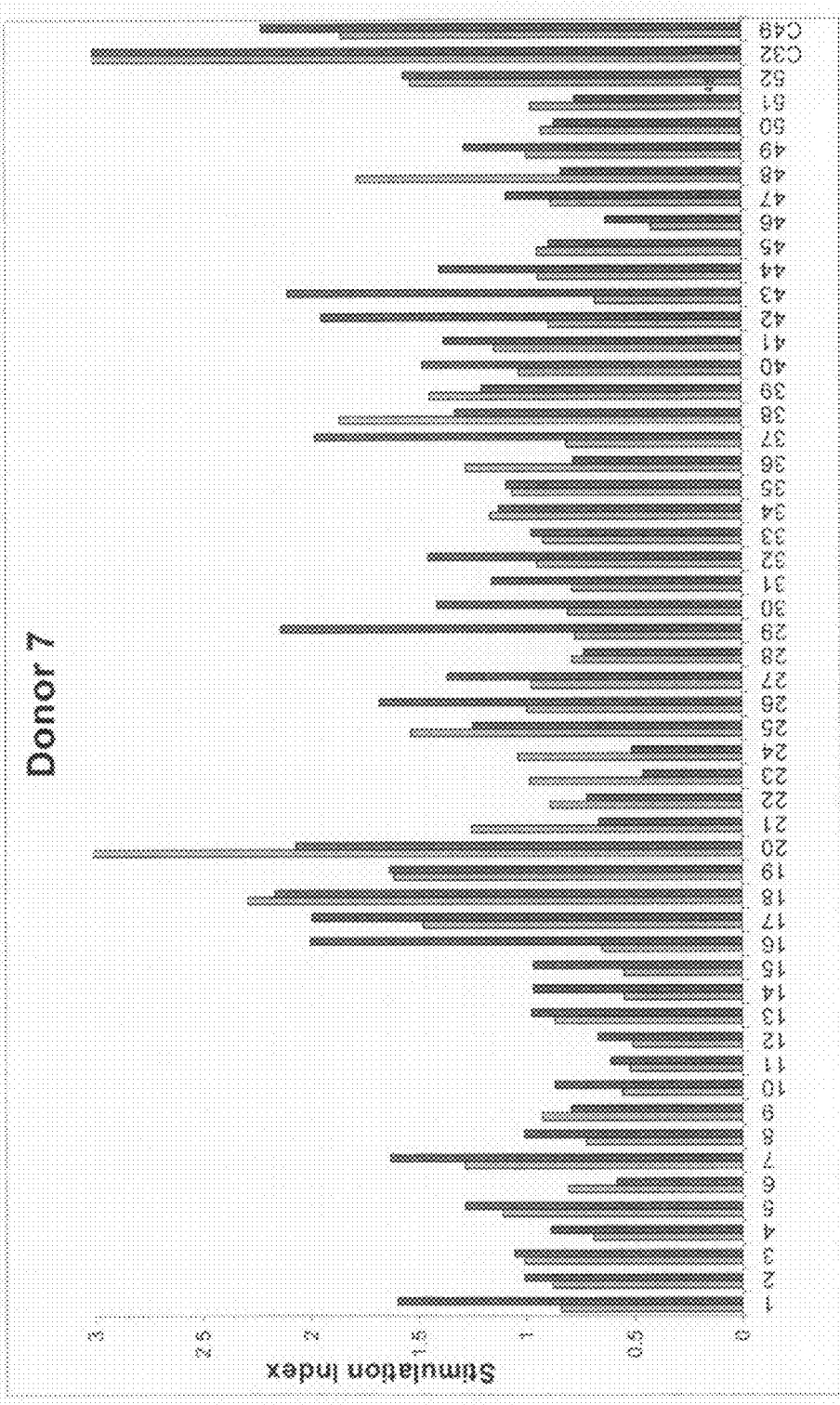
FIG. 7, Panel e

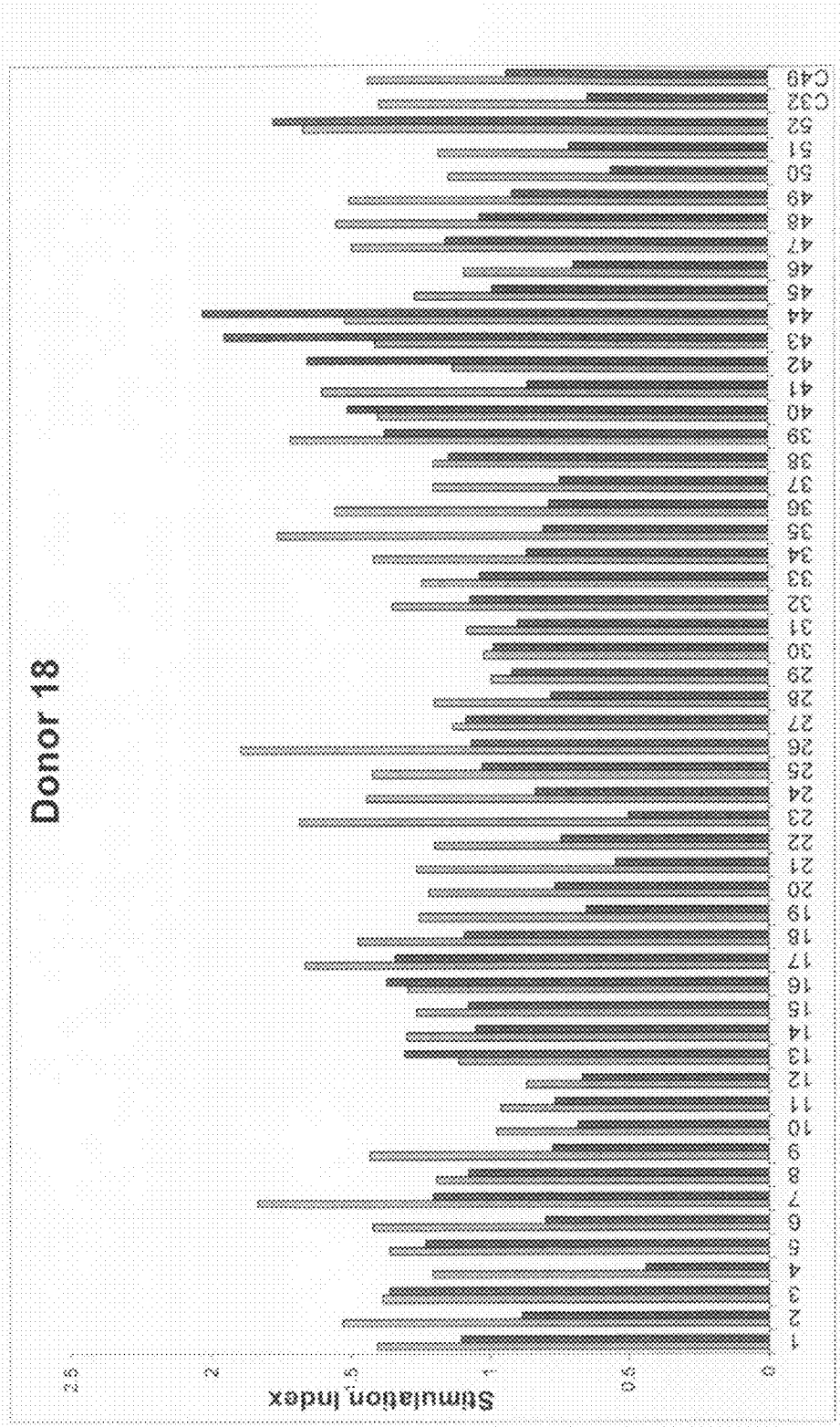
FIG. 7, Panel f

FIGURE 8

INFβ IMMUNOGENIC REGIONS

REGION 1 (R1)

```
        Residue#    49                      72
(SEQ ID NO: 2)      QFQKEDAALTIYEMLQNIFAIFRQ Stimulating
        Peptides:
            #17    QFQKEDAALTIYEML   (SEQ ID NO: 107)
            #18        KEDAALTIYEMLQNI   (SEQ ID NO: 108)
            #19            AALTIYEMLQNIFAI   (SEQ ID NO: 109)
            #20                TIYEMLQNIFAIFRQ   (SEQ ID NO: 110)
```

R1 Cumulative Stimulation Index from responsive donors ≥ 8

REGION 2 (R2)

```
        Residue # 124                    145
(SEQ ID NO: 3)      RYYGRILHYLKAKEYSHCAWT Stimulating
        Peptides:
            #42    RYYGRILHYLKA (SEQ ID NO: 132)
            #43        GRILHYLKAKEY (SEQ ID NO: 133)
            #44            LHYLKAKEYSHC (SEQ ID NO: 134)
            #45                LKAKEYSHCAWT (SEQ ID NO: 135)
```

R2 Cumulative Stimulation Index from responsive donors ≥ 10
Cumulative Stimulation Index for underlined residues in
responsive donors ≥ 9

FIGURE 9

| Donor # | Overlapping Epitope* | | | Single peptide Epitope** | |
|---|---|---|---|---|---|
| | Number of peptides | Peptide ID# | Epitope Region | Peptide ID# | Epitope Region |
| 1 | 1 | | | 21 | R1 |
| 1 | 2 | 43, 44 | R2 | | |
| 2 | 1 | | | 23 | R1 |
| 3 | 1 | | | 45 | R2 |
| 5 | 1 | | | 44 | R2 |
| 7 | 3 | 17, 18, 20 | R1 | | |
| 7 | 1 | | | 43 | R2 |
| 18 | 1 | | | 44 | R2 |

FIGURE 10, Panel a
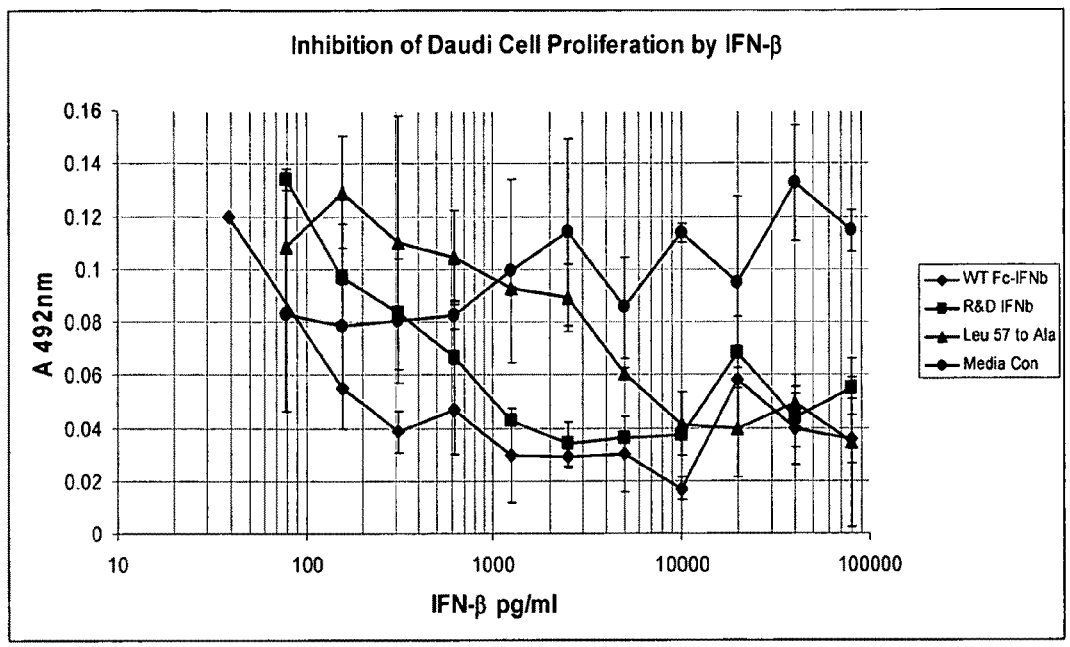
FIGURE 10, Panel b
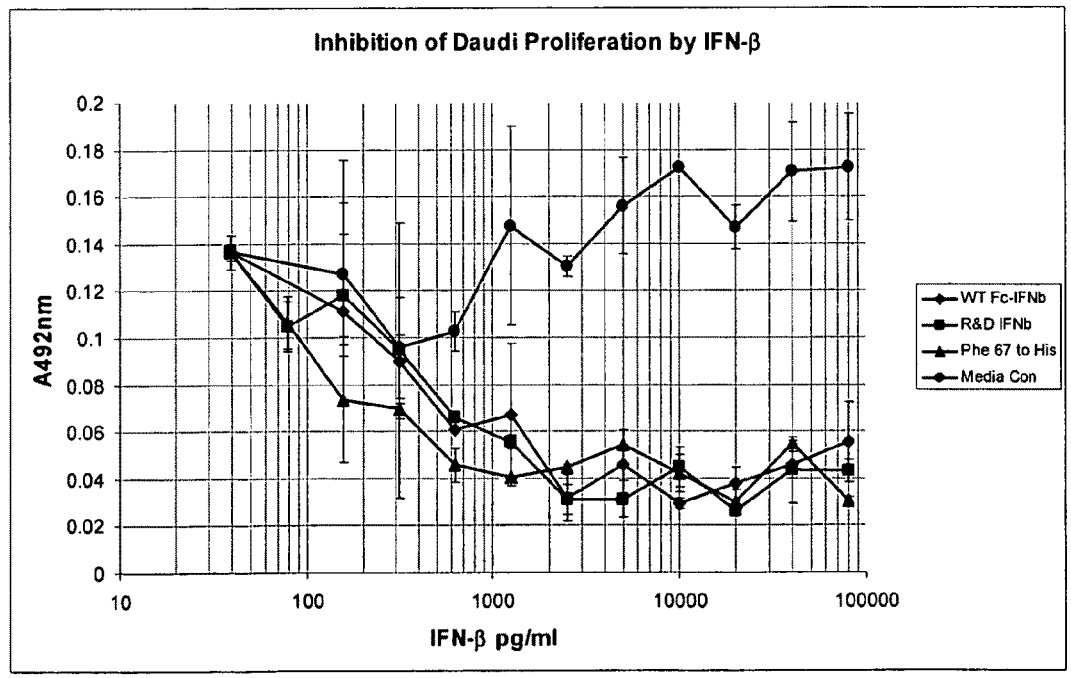

MODIFIED INTERFERON BETA WITH REDUCED IMMUNOGENICITY

CROSS-REFERENCE TO RELATED APPLICATIONS

This application is a divisional of U.S. Ser. No. 10/471,894 filed on Sep. 12, 2003 now U.S. Pat. No. 7,381,795, which is the National Stage of International Application No. PCT/EP2002/02925, filed on Mar. 15, 2002, which claims priority from European Patent No. 01106539.8, filed on Mar. 15, 2001, each of which is incorporated herein by reference in its entirety.

FIELD OF THE INVENTION

The present invention relates to polypeptides to be administered especially to humans and in particular for therapeutic use. The polypeptides are modified polypeptides whereby the modification results in a reduced propensity for the polypeptide to elicit an immune response upon administration to the human subject. The invention in particular relates to the modification of human interferon and specifically human interferon beta (INFβ) to result in INFβ protein variants that are substantially non-immunogenic or less immunogenic than any non-modified counterpart when used in vivo. The invention relates furthermore to T-cell epitope peptides derived from said non-modified protein by means of which it is possible to create modified INFβ variants with reduced immunogenicity.

BACKGROUND OF THE INVENTION

There are many instances whereby the efficacy of a therapeutic protein is limited by an unwanted immune reaction to the therapeutic protein. Several mouse monoclonal antibodies have shown promise as therapies in a number of human disease settings but in certain cases have failed due to the induction of significant degrees of a human anti-murine antibody (HAMA) response (Schroff, R. W. et al. (1985) *Cancer Res.* 45: 879-885; Shawler, D. L. et al. (1985) *J. Immunol.* 135: 1530-1535). For monoclonal antibodies, a number of techniques have been developed in attempt to reduce the HAMA response (WO 89/09622; EP 0239400; EP 0438310; WO 91/06667). These recombinant DNA approaches have generally reduced the mouse genetic information in the final antibody construct whilst increasing the human genetic information in the final construct. Notwithstanding, the resultant "humanized" antibodies have, in several cases, still elicited an immune response in patients (Issacs J. D. (1990) *Sem. Immunol.* 2: 449, 456; Rebello, P. R. et al. (1999) *Transplantation* 68: 1417-1420).

Antibodies are not the only class of polypeptide molecule administered as a therapeutic agent against which an immune response may be mounted. Even proteins of human origin and with the same amino acid sequences as occur within humans can still induce an immune response in humans. Notable examples include the therapeutic use of granulocyte-macrophage colony stimulating factor (Wadhwa, M. et al. (1999) *Clin. Cancer Res.* 5: 1353-1361) and interferon alpha 2 (Russo, D. et al. (1996) *Bri. J. Haem.* 94: 300-305; Stein, R. et al. (1988) *New Engl. J. Med.* 318: 1409-1413) amongst others.

A principal factor in the induction of an immune response is the presence within the protein of peptides that can stimulate the activity of T-cells via presentation on MHC Class II molecules, so-called "T-cell epitopes". Such potential T-cell epitopes are commonly defined as any amino acid residue sequence with the ability to bind to MHC Class II molecules. Such T-cell epitopes can be measured to establish MHC binding. Implicitly, a "T-cell epitope" means an epitope which when bound to MHC molecules can be recognized by a T-cell receptor (TCR), and which can, at least in principle, cause the activation of these T-cells by engaging a TCR to promote a T-cell response. It is, however, usually understood that certain peptides which are found to bind to MHC Class II molecules may be retained in a protein sequence because such peptides are recognized as "self" within the organism into which the final protein is administered.

It is known, that certain of these T-cell epitope peptides can be released during the degradation of peptides, polypeptides or proteins within cells and subsequently be presented by molecules of the major histocompatability complex (MHC) in order to trigger the activation of T-cells. For peptides presented by MHC Class II, such activation of T-cells can then give rise, for example, to an antibody response by direct stimulation of B-cells to produce such antibodies.

MHC Class II molecules are a group of highly polymorphic proteins which play a central role in helper T-cell selection and activation. The human leukocyte antigen group DR (HLA-DR) are the predominant isotype of this group of proteins and are the major focus of the present invention. However, isotypes HLA-DQ and HLA-DP perform similar functions, hence the present invention is equally applicable to these. The MHC Class II DR molecule is made of an alpha and a beta chain which insert at their C-termini through the cell membrane. Each hetero-dimer possesses a ligand binding domain which binds to peptides varying between 9 and 20 amino acids in length, although the binding groove can accommodate a maximum of 11 amino acids. The ligand binding domain is comprised of amino acids 1 to 85 of the alpha chain, and amino acids 1 to 94 of the beta chain. DQ molecules have recently been shown to have an homologous structure and the DP family proteins are also expected to be very similar. In humans approximately 70 different allotypes of the DR isotype are known, for DQ there are 30 different allotypes and for DP 47 different allotypes are known. Each individual bears two to four DR alleles, two DQ and two DP alleles. The structure of a number of DR molecules has been solved and such structures point to an open-ended peptide binding groove with a number of hydrophobic pockets which engage hydrophobic residues (pocket residues) of the peptide (Brown et al. *Nature* (1993) 364: 33; Stern et al. (1994) *Nature* 368: 215). Polymorphism identifying the different allotypes of class II molecule contributes to a wide diversity of different binding surfaces for peptides within the peptide binding grove and at the population level ensures maximal flexibility with regard to the ability to recognize foreign proteins and mount an immune response to pathogenic organisms.

There is a considerable amount of polymorphism within the ligand binding domain with distinct "families" within different geographical populations and ethnic groups. This polymorphism affects the binding characteristics of the peptide binding domain, thus different "families" of DR molecules will have specificities for peptides with different sequence properties, although there may be some overlap. This specificity determines recognition of Th-cell epitopes (Class II T-cell response) which are ultimately responsible for driving the antibody response to B-cell epitopes present on the same protein from which the Th-cell epitope is derived. Thus, the immune response to a protein in an individual is heavily influenced by T-cell epitope recognition which is a function of the peptide binding specificity of that individual's HLA-DR allotype. Therefore, in order to identify T-cell epitopes within a protein or peptide in the context of a global population, it is desirable to consider the binding properties of as diverse a set of HLA-DR allotypes as possible, thus covering as high a percentage of the world population as possible.

An immune response to a therapeutic protein such as INFβ proceeds via the MHC Class II peptide presentation pathway. Here exogenous proteins are engulfed and processed for presentation in association with MHC Class II molecules of the DR, DQ or DP type. MHC Class II molecules are expressed by professional antigen presenting cells (APCs), such as macrophages and dendritic cells amongst others. Engagement of a MHC Class II peptide complex by a cognate T-cell receptor on the surface of the T-cell, together with the cross-binding of certain other co-receptors such as the CD4 molecule, can induce an activated state within the T-cell. Activation leads to the release of cytokines further activating other lymphocytes such as B cells to produce antibodies or activating T killer cells as a full cellular immune response.

The ability of a peptide to bind a given MHC Class II molecule for presentation on the surface of an APC is dependent on a number of factors most notably its primary sequence. This will influence both its propensity for proteolytic cleavage and also its affinity for binding within the peptide binding cleft of the MHC Class II molecule. The MHC Class II/peptide complex on the APC surface presents a binding face to a particular T-cell receptor (TCR) able to recognize determinants provided both by exposed residues of the peptide and the MHC Class II molecule.

In the art there are procedures for identifying synthetic peptides able to bind MHC Class II molecules (e.g. WO98/52976 and WO00/34317). Such peptides may not function as T-cell epitopes in all situations, particularly, in vivo due to the processing pathways or other phenomena. T-cell epitope identification is the first step to epitope elimination. The identification and removal of potential T-cell epitopes from proteins has been previously disclosed. In the art methods have been provided to enable the detection of T-cell epitopes usually by computational means scanning for recognized sequence motifs in experimentally determined T-cell epitopes or alternatively using computational techniques to predict MHC Class II-binding peptides and in particular DR-binding peptides.

WO98/52976 and WO00/34317 teach computational threading approaches to identifying polypeptide sequences with the potential to bind a sub-set of human MHC Class II DR allotypes. In these teachings, predicted T-cell epitopes are removed by the use of judicious amino acid substitution within the primary sequence of the therapeutic antibody or non-antibody protein of both non-human and human derivation.

Other techniques exploiting soluble complexes of recombinant MHC molecules in combination with synthetic peptides and able to bind to T-cell clones from peripheral blood samples from human or experimental animal subjects have been used in the art (Kern, F. et al. (1998) *Nature Medicine* 4:975-978; Kwok, W. W. et al. (2001) *TRENDS in Immunol.* 22:583-588). These and other schemes including for example the use of whole INFβ proteins or INFβ derived synthetic peptides or variant molecules thereof which are screened for molecules with altered ability to bind or stimulate T-cells may also be exploited in an epitope identification strategy.

As depicted above and as consequence thereof, it would be desirable to identify and to remove or at least to reduce T-cell epitopes from a given in principal therapeutically valuable but originally immunogenic peptide, polypeptide or protein.

One of these therapeutically valuable molecules is INFβ. The molecule is a single chain glycoprotein of 166 amino acid residues with important biological and immunological activity. The protein has significant therapeutic potential in man as an anti-viral, anti-proliferative and immunomodulating agent. There are a number of commercial sources of recombinant INFβ and these include AVONEX® recombinant INFβ, manufactured by Biogen, Inc. (Cambridge, Mass., USA); REBIF® recombinant INFβ manufactured by Serono Internationa (Geneva, Switzerland); and BETASERON® recombinant INFβ produced by the Chiron Corporation (Emeryville, Calif., USA). The amino acid sequences of AVONEX® recombinant INFβ and REBIF® recombinant INFβ are identical to that of natural human INFβ and both products are glycosylated. By contrast, BETASERON® recombinant INFβ is produced from an *E. coli* expression host and is a mutated form of INFβ where cysteine 17 has been mutated to a serine residue. It is a 165 amino acid non-glycosylated protein with a molecular weight of 18500.

The mature human INFβ protein is single polypeptide of 166 amino acids with a molecular weight of 22500 and is produced by various cell types including fibroblasts and macrophages. The amino acid sequence of human INFβ (depicted as one-letter code) is as follows:

(SEQ ID NO: 1)
MSYNLLGFLQRSSNFQCQKLLWQLNGRLEYCLKDRMNFDIPEEIKQLQQF

QKEDAALTIYEMLQNIFAIFRQDSSSTGWNETIVENLLANVYHQINHLKT

VLEEKLEKEDFTRGKLMSSLHLKRYYGRILHYLKAKEYSHCAWTIVRVEI

LRNFYFINRLTGYLRN.

Others have provided INFβ molecules, including modified IFNβ such as the mutated and aglycosylated form comprising BETASERON® recombinant INFβ and the series of alanine scanning mutants described by Runkel et al. (Runkel, L. et al. (2000) *Biochemistry* 39: 2538-2551). Other examples include those disclosed in U.S. Pat. No. 4,588,585 and U.S. Pat. No. 6,127,332 but none of these teachings recognise the importance of T cell epitopes to the immunogenic properties of the protein nor have been conceived to directly influence said properties in a specific and controlled way according to the scheme of the present invention.

However, there is a continued need for INFβ analogues with enhanced properties. Desired enhancements include alternative schemes and modalities for the expression and purification of the said therapeutic, but also and especially, improvements in the biological properties of the protein. There is a particular need for enhancement of the in vivo characteristics when administered to the human subject. In this regard, it is highly desired to provide INFβ with reduced or absent potential to induce an immune response in the human subject.

SUMMARY OF THE INVENTION

The present invention provides for modified forms of human interferon beta 1a, herein called "INFβ", in which the immune characteristic is modified by means of reduced or removed numbers of potential T-cell epitopes.

The invention discloses sequences identified within the INFβ primary sequence that are potential T-cell epitopes by virtue of MHC Class II binding potential. This disclosure specifically pertains the human INFβ protein being 166 amino acid residues.

The invention discloses also specific positions within the primary sequence of the molecule which according to the invention are to be altered by specific amino acid substitution, addition or deletion whilst retaining to a maximum degree the biological activity of the protein. In cases in which the loss of immunogenicity can be achieved only by a simultaneous loss of biological activity it is possible to restore said activity by further alterations within the amino acid sequence of the protein.

The invention furthermore discloses methods to produce such modified molecules, and above all methods to identify said T-cell epitopes which require alteration in order to reduce or remove immunogenic sites.

The protein according to this invention would expect to display an increased circulation time within the human subject and would be of particular benefit in chronic or recurring disease settings such as is the case for a number of indications for INFβ. The present invention provides for modified forms of INFβ proteins that are expected to display enhanced properties in vivo. The present invention discloses the major regions of the INFβ primary sequence that are immunogenic in man and provides modification to the said sequences to eliminate or reduce the immunogenic effectiveness of these sites. In one embodiment, synthetic peptides comprising the said immunogenic regions can be provided in pharmaceutical composition for the purpose of promoting a tolerogenic response to the whole molecule. In a further embodiment, the modified INFβ molecules of the present invention can be used in pharmaceutical compositions.

In summary the invention relates to the following issues:

a modified molecule having the biological activity of INFβ and being substantially non-immunogenic or less immunogenic than any non-modified molecule having the same biological activity when used in vivo;

an accordingly specified molecule, wherein said loss of immunogenicity is achieved by removing one or more T-cell epitopes derived from the originally non-modified molecule;

an accordingly specified molecule, wherein said loss of immunogenicity is achieved by reduction in numbers of MHC allotypes able to bind peptides derived from said molecule;

an accordingly specified molecule, wherein one T-cell epitope is removed;

an accordingly specified molecule, wherein said originally present T-cell epitopes are MHC Class II ligands or peptide sequences which show the ability to stimulate or bind T-cells via presentation on class II;

an accordingly specified molecule, wherein said peptide sequences are selected from the group as depicted in FIG. 1;

an accordingly specified molecule, wherein 1-9 amino acid residues, preferably one amino acid residue in any of the originally present T-cell epitopes are altered;

an accordingly specified molecule, wherein the alteration of the amino acid residues is substitution, addition or deletion of originally present amino acid(s) residue(s) by other amino acid residue(s) at specific position(s);

an accordingly specified molecule, wherein one or more of the amino acid residue substitutions are carried out as indicated in FIG. 2;

an accordingly specified molecule, wherein (additionally) one or more of the amino acid residue substitutions are carried out as indicated in FIG. 3 for the reduction in the number of MHC allotypes able to bind peptides derived from said molecule;

an accordingly specified molecule, wherein one or more amino acid residue substitutions are carried out as indicted in FIG. 4;

an accordingly specified molecule, wherein, if necessary, additionally further alteration usually by substitution, addition or deletion of specific amino acid(s) is conducted to restore biological activity of said molecule;

an accordingly specified molecule wherein alteration is conducted at one or more residues from the string of contiguous residues of sequence (a) QFQKEDAALTIYEMLQNIFAIFRQ (R1, SEQ ID NO: 2) and/or of sequence; (b) RYYGRILHYLKAKEYSHCAWT (R2, SEQ ID NO: 3) wherein said sequences are derived from the INFβ wild-type sequence;

a peptide molecule comprising 13-15 consecutive residues from any of sequences (a) or (b) above;

a peptide molecule comprising at least 9 consecutive residues from any of the sequences (a) or (b) above;

a peptide molecule of above sharing greater than 90% amino acid identity with any of the peptide sequences derived from (a) or (b) above;

a peptide molecule of above sharing greater than 80% amino acid identity with any of the peptide sequences derived from (a) or (b) above;

peptide sequences as above able to bind MHC Class II;

an accordingly specified INFβ molecule, wherein one or more of the amino acid substitutions is conducted at a position corresponding to any of the amino acids specified within sequence (a) above;

an accordingly specified INFβ molecule, wherein one or more of the amino acid substitutions is conducted at a position corresponding to any of the amino acids specified within sequence (b) above;

an accordingly specified INFβ molecule, wherein one or more of the amino acid substitutions is conducted at a position corresponding to any of the amino acids specified within sequences (a) or (b) above;

a modified human interferon beta (INFβ) having reduced immunogenicity consisting of the following sequence:

```
                                              (SEQ ID NO: 4)
MSYNLLGFLQRSSNFQX⁰QKLLWQLNGRLEYCLKDRMNFDIPEEIKQLQQ

X¹QKEDAAX²TX³X⁴EX⁵X⁶QNX⁷X⁸AX⁹X¹⁰RQDSSSTGWNETIVENLL

ANVYHQINHLKTVLEEKLEKEDFTRGKLMSSLHLKRYYGRILHYLKAKEY

SHCAWTIVRVEILRNFYFINRLTGYLRN,
``` wherein $X^0$ is C, S; $X^1$ is F, A; $X^2$ is L, A; $X^3$ is I, A; $X^4$ is Y, N; $X^5$ is M, A; $X^6$ is L, A; $X^7$ is 1, T; $X^8$ is F, H; $X^9$ is I, A and $X^{10}$ is F, A;

whereby simultaneously $X^1$=F, $X^2$=L, $X^3$=I, $X^4$=Y, $X^5$=M, $X^6$=L, $X^7$=1, $X^8$=F, $X^9$=I and $X^{10}$=F are excluded (these exclusions describe the known imungenetically non-modified INFβ variants);

a modified human interferon beta (INFβ) having reduced immunogenicity consisting of the following sequence:

```
                                              (SEQ ID NO: 5)
MSYNLLGFLQRSSNFQX⁰QKLLWQLNGRLEYCLKDRMNFDIPEEIKQLQQ

FQKEDAALTIYEMLQNIFAIFRQDSSSTGWNETIVENLLANVYHQINHLK

TVLEEKLEKEDFTRGKLMSSLHLKRX¹X²GRX³X⁴HX⁵X⁶KAKEX⁷SHCA

WTIVRVEILRNFYFINRLTGYLRN,
``` wherein $X^0$ is C, S; $X^1$ is Y, A; $X^2$ is Y, A; $X^3$ is I, A; $X^4$ is L, A; $X^5$ is Y, S; $X^6$ is L, A and $X^7$ is Y, H, A; whereby simultaneously $X^1$=Y, $X^2$=y, $X^3$=1, $X^4$=L, $X^1$=y, $X^6$=L and $X^7$=Y are excluded (these exclusions describe the known imungenetically non-modified INFβ variants);

an INF beta molecule consisting of 9-15 consecutive amino acid residues, having a potential MHC Class II binding activity and created from the primary sequence of non-modified INFβ, whereby said molecule has a stimulation index of at least 1.8, preferably 1.8-2, more preferably >2, in a biological assay of cellular proliferation wherein said index is taken as the value of cellular proliferation scored following stimulation by a peptide and divided by the value of cellular proliferation scored in control cells not in receipt peptide and wherein cellular proliferation is measured by any suitable means;

a pharmaceutical composition comprising any of the peptides or modified peptides of above having the activity of binding to MHC Class II;

a DNA sequence or molecule which codes for any of said specified modified molecules as defined above and below;

a pharmaceutical composition comprising a modified molecule having the biological activity of INFβ;

a pharmaceutical composition as defined above and/or in the claims, optionally together with a pharmaceutically acceptable carrier, diluent or excipient;

a method for manufacturing a modified molecule having the biological activity of INFβ as defined in any of the claims of the above-cited claims comprising the following steps: (i) determining the amino acid sequence of the polypeptide or part thereof; (ii) identifying one or more potential T-cell epitopes within the amino acid sequence of the protein by any method including determination of the binding of the peptides to MHC molecules using in vitro or in silico techniques or biological assays; (iii) designing new sequence variants with one or more amino acids within the identified potential T-cell epitopes modified in such a way to substantially reduce or eliminate the activity of the T-cell epitope as determined by the binding of the peptides to MHC molecules using in vitro or in silico techniques or biological assays; (iv) constructing such sequence variants by recombinant DNA techniques and testing said variants in order to identify one or more variants with desirable properties; and (v) optionally repeating steps (ii)-(iv);

an accordingly specified method, wherein step (iii) is carried out by substitution, addition or deletion of 1-9 amino acid residues in any of the originally present T-cell epitopes;

an accordingly specified method, wherein the alteration is made with reference to an homologous protein sequence and/or in silico modeling techniques;

an accordingly specified method, wherein step (ii) of above is carried out by the following steps: (a) selecting a region of the peptide having a known amino acid residue sequence; (b) sequentially sampling overlapping amino acid residue segments of predetermined uniform size and constituted by at least three amino acid residues from the selected region; (c) calculating MHC Class II molecule binding score for each said sampled segment by summing assigned values for each hydrophobic amino acid residue side chain present in said sampled amino acid residue segment; and (d) identifying at least one of said segments suitable for modification, based on the calculated MHC Class II molecule binding score for that segment, to change overall MHC Class II binding score for the peptide without substantially reducing therapeutic utility of the peptide; step (c) is preferably carried out by using a Böhm scoring function modified to include 12-6 van der Waal's ligand-protein energy repulsive term and ligand conformational energy term by (1) providing a first data base of MHC Class II molecule models; (2) providing a second data base of allowed peptide backbones for said MHC Class II molecule models; (3) selecting a model from said first data base; (4) selecting an allowed peptide backbone from said second data base; (5) identifying amino acid residue side chains present in each sampled segment; (6) determining the binding affinity value for all side chains present in each sampled segment; and repeating steps (1) through (5) for each said model and each said backbone;

a 13mer T-cell epitope peptide having a potential MHC Class II binding activity and created from non-modified INFβ, selected from the group as depicted in FIG. 1 and its use for the manufacture of INFβ having substantially no or less immunogenicity than any non-modified molecule with the same biological activity when used in vivo;

a peptide sequence consisting of at least 9 consecutive amino acid residues of a 13mer T-cell epitope peptide as specified above and its use for the manufacture of INFβ having substantially no or less immunogenicity than any non-modified molecule and having the biological activity of a human interferon β when used in vivo;

a 13mer T-cell epitope peptide having a potential MHC Class II binding activity and created from non-modified INFβ, selected from any of the group of sequences (a) or (b) as defined above and its use for the manufacture of INFβ having substantially no or less immunogenicity than any non-modified molecule and having the biological activity of a human interferon β when used in vivo;

a peptide sequence consisting of at least 9 consecutive amino acid residues of a 13mer T-cell epitope peptide as derived from any of the sequences (a) or (b) as specified above, and its use for the manufacture of INFβ having substantially no or less immunogenicity than any non-modified molecule and having the biological activity of a human interferon β when used in vivo.

BRIEF DESCRIPTION OF THE DRAWINGS

FIG. 1 provides a table of peptide sequences in human INFβ with potential human MHC Class II binding activity. Peptides are 13mers, amino acids are identified using single letter code.

FIG. 2 provides a table detailing amino acid substitutions leading to the elimination of T-cell epitopes of human INFβ. WT=wild type residue.

FIG. 3 provides a table detailing additional substitutions leading to the removal of a potential T-cell epitope for 1 or more MHC allotypes.

FIG. 4 provides a table of preferred substitutions in human INFβ. WT=wild type residue; #=position; MUT=desired residue. The table indicates the epitope region (R1 or R2) in which each substitution is located.

FIG. 5 provides a table of the INFβ 15-mer peptide sequences analyzed using the naïve human in vitro T-cell assay of EXAMPLE 2. The peptide ID#, SEQ ID NO, and position of the N-terminal peptide residue of each potential epitope sequence within the INFβ sequence is indicated.

FIG. 6 shows cumulative stimulation indexes from 6 individuals that respond to stimulation with INFβ peptides. Panel 6a shows results following stimulation using peptides at 1 μM concentration. Panel 6b shows results following stimulation using peptides at 10 μM concentration. Six donors from 20 screened responded to stimulation with one or more peptides from the INFβ sequence. Responses to individual peptides are grouped into two distinct regions R1 and R2. Control peptides C32 (DRB1-restricted) and C49 (DP-restricted) are included for comparison. Cross-hatching within each bar indicates the contribution from individual donors. SI=stimulation index.

FIG. 7 shows the donor specific stimulation responses to the INFβ synthetic peptides. Panels 7a-7f show individual donor responses to peptides at 1 μM (light bars) and 10 μM (dark bars) final peptide concentration. Data from control peptides C32 (DRB1-restricted) and C49 (DP-restricted) are included in each panel for comparison. Threshold for positive stimulation index=2.

FIG. 8 shows the immunogenic regions within INFβ and details the peptide sequences from these regions able to stimulate naïve human T-cells.

FIG. 9 provides a table indicating INFβ peptides capable of promoting proliferation of naïve human T-cells in vitro. For two of the donors, responses are recorded to multiple overlapping peptides from either epitope region R1 or R2. Responses to individual synthetic peptides mapping to epitope regions R1 or R2 are scored from six donors.

FIG. 10 provides representative data of the anti-proliferative effect of two modified INFβ molecules. Assays were conducted according to the methods of EXAMPLE 4. In each of panels a) and b), antiproliferative effects of control treatments are recorded. Controls comprise non-modified INFβ-Fc fusion=WT-FcINFβ; a standard INFβ preparation=R&D IFNβ and media containing no INF=Media Con. Panel a) shows data for Leu 57 Ala (INFβ-BIOV7) modified INFβ. Panel b) shows data for the Phe 67 His (INFβ-BIOV12) modified INFβ.

DETAILED DESCRIPTION OF THE INVENTION

The term "T-cell epitope" means according to the understanding of this invention an amino acid sequence which is able to bind MHC Class II, able to stimulate T-cells and/or also to bind (without necessarily measurably activating) T-cells in complex with MHC Class II.

The term "peptide" as used herein and in the appended claims, is a compound that includes two or more amino acids. The amino acids are linked together by a peptide bond (defined herein below). There are 20 different naturally occurring amino acids involved in the biological production of peptides, and any number of them may be linked in any order to form a peptide chain or ring. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Some peptides contain only a few amino acid units. Short peptides, e.g., having less than ten amino acid units, are sometimes referred to as "oligopeptides". Other peptides contain a large number of amino acid residues, e.g. up to 100 or more, and are referred to as "polypeptides". By convention, a "polypeptide" may be considered as any peptide chain containing three or more amino acids, whereas a "oligopeptide" is usually considered as a particular type of "short" polypeptide. Thus, as used herein, it is understood that any reference to a "polypeptide" also includes an oligopeptide. Further, any reference to a "peptide" includes polypeptides, oligopeptides, and proteins. Each different arrangement of amino acids forms different polypeptides or proteins. The number of polypeptides—and hence the number of different proteins—that can be formed is practically unlimited.

"Alpha carbon (Cα)" is the carbon atom of the carbon-hydrogen (CH) component that is in the peptide chain. A "side chain" is a pendant group to Cα that can comprise a simple or complex group or moiety, having physical dimensions that can vary significantly compared to the dimensions of the peptide.

The invention may be applied to any INFβ species of molecule with substantially the same primary amino acid sequences as those disclosed herein and would include therefore INFβ molecules derived by genetic engineering means or other processes and may contain more or less than 166 amino acid residues.

INFβ proteins such as identified from other mammalian sources have in common many of the peptide sequences of the present disclosure and have in common many peptide sequences with substantially the same sequence as those of the disclosed listing. Such protein sequences equally therefore fall under the scope of the present invention.

The invention is conceived to overcome the practical reality that soluble proteins introduced into autologous organisms can trigger an immune response resulting in development of host antibodies that bind to the soluble protein. A prominent example of this phenomenon amongst others, is the clinical use of interferon alpha 2 (INFα2). A significant proportion of human patients treated with INFα2 make antibodies despite the fact that this protein is produced endogenously (Russo, D. et al. (1996) ibid; Stein, R. et al. (1988) ibid). It is known that the clinical use of INFβ has also resulted in the development of immune responses to the INFβ despite the fact that a molecule of at least identical primary structure is produced endogenously in man (Kivisakk, P. et al. (2000) *Eur. J. Neurol.* 7: 27-34; Myhr, K. M. et al. (2000) *Neurology* 55: 1569-1572). The present invention seeks to address this by providing INFβ proteins with altered propensity to elicit an immune response on administration to the human host. According to the methods described herein, the inventors have discovered and now disclose the regions of the INFβ molecule comprising the critical T-cell epitopes driving the immune responses to this autologous protein.

The general method of the present invention leading to the modified INFβ comprises the following steps:

(a) determining the amino acid sequence of the polypeptide or part thereof;

(b) identifying one or more potential T-cell epitopes within the amino acid sequence of the protein by any method including determination of the binding of the peptides to MHC molecules using in vitro or in silico techniques or biological assays;

(c) designing new sequence variants with one or more amino acids within the identified potential T-cell epitopes modified in such a way to substantially reduce or eliminate the activity of the T-cell epitope as determined by the binding of the peptides to MHC molecules using in vitro or in silico techniques or biological assays. Such sequence variants are created in such a way to avoid creation of new potential T-cell epitopes by the sequence variations unless such new potential T-cell epitopes are, in turn, modified in such a way to substantially reduce or eliminate the activity of the T-cell epitope; and (d) constructing such sequence variants by recombinant DNA techniques and testing said variants in order to identify one or more variants with desirable properties according to well known recombinant techniques.

The identification of potential T-cell epitopes according to step (b) can be carried out according to methods describes previously in the prior art. Suitable methods are disclosed in WO 98/59244; WO 98/52976; WO 00/34317 and may preferably be used to identify binding propensity of INFβ-derived peptides to an MHC Class II molecule.

Another very efficacious method for identifying T-cell epitopes by calculation is described in the EXAMPLE 1 which is a preferred embodiment according to this invention.

In practice a number of variant INFβ proteins will be produced and tested for the desired immune and functional characteristic. The variant proteins will most preferably be produced by recombinant DNA techniques although other procedures including chemical synthesis of INFβ fragments may be contemplated. Chemical synthesis is for example particularly preferred for the production of short INFβ fragments such as the R1 or R2 sequence elements disclosed herein and which comprise a particular embodiment of the present invention.

The results of an analysis according to step (b) of the above scheme and pertaining to the human INFβ protein sequence of 166 amino acid residues is presented in FIG. 1. The results of a design and constructs according to step (c) and (d) of the above scheme and pertaining to the modified molecule of this invention is presented in FIG. 2 and FIG. 3.

The invention relates to INFβ analogues in which substitutions of at least one amino acid residue have been made at positions resulting in a substantial reduction in activity of or elimination of one or more potential T-cell epitopes from the protein. One or more amino acid substitutions at particular points within any of the potential MHC Class II ligands identified in FIG. 1 may result in a INFβ molecule with a reduced immunogenic potential when administered as a therapeutic to the human host.

It is most preferred to provide an INFβ molecule in which amino acid modification (e.g. a substitution) is conducted within the most immunogenic regions of the parent molecule. The inventors herein have discovered that the most immunogenic regions of the INF1 molecule in man are confined to two regions R1 and R2 comprising respectively amino acid sequences; QFQKEDAALTIYEMLQNIFAIFRQ (SEQ ID NO: 2) and RYYGRILHYLKAKEYSHCAWT (SEQ ID NO: 3), respectively. The major preferred embodiments of the present invention comprise INFβ molecules for which the MHC Class II ligands of FIG. 1 and which align either in their entirety or to a minimum of 9 amino acid residues with any of the above sequence elements R1 or R2 are altered such as to eliminate binding or otherwise reduce the numbers of MHC allotypes to which the peptide can bind.

The preferred embodiments of the invention include the specific substitutions of FIG. 4. It is particularly preferred to provide modified INFβ molecules containing combinations of substitutions from FIG. 4. Combinations which comprise multiple (greater than 1) modification both within each of the immunogenic regions R1 and R2, and combinations comprising multiple modifications to both R1 and R2 within the same molecule are especially preferred although such preference is not intended to limit the combinations of substitution which are considered desirable.

For the elimination of T-cell epitopes, amino acid substitutions are preferably made at appropriate points within the peptide sequence predicted to achieve substantial reduction or elimination of the activity of the T-cell epitope. In practice an appropriate point will preferably equate to an amino acid residue binding within one of the pockets provided within the MHC Class II binding groove.

It is most preferred to alter binding within the first pocket of the cleft at the so-called P1 or P1 anchor position of the peptide. The quality of binding interaction between the P1 anchor residue of the peptide and the first pocket of the MHC Class II binding groove is recognized as being a major determinant of overall binding affinity for the whole peptide. An appropriate substitution at this position of the peptide will be for a residue less readily accommodated within the pocket, for example, substitution to a more hydrophilic residue. Amino acid residues in the peptide at positions equating to binding within other pocket regions within the MHC binding cleft are also considered and fall under the scope of the present.

It is understood that single amino acid substitutions within a given potential T-cell epitope are the most preferred route by which the epitope may be eliminated. Combinations of substitution within a single epitope may be contemplated and for example can be particularly appropriate where individually defined epitopes are in overlap with each other. Moreover, amino acid substitutions either singly within a given epitope or in combination within a single epitope may be made at positions not equating to the "pocket residues" with respect to the MHC Class II binding groove, but at any point within the peptide sequence. Substitutions may be made with reference to an homologues structure or structural method produced using in silico techniques known in the art and may be based on known structural features of the molecule according to this invention. All such substitutions fall within the scope of the present invention.

Amino acid substitutions other than within the peptides identified above may be contemplated particularly when made in combination with substitution(s) made within a listed peptide. For example a change may be contemplated to restore structure or biological activity of the variant molecule. Such compensatory changes and changes to include deletion or addition of particular amino acid residues from the INFβ polypeptide resulting in a variant with desired activity and in combination with changes in any of the disclosed peptides fall under the scope of the present.

In as far as this invention relates to modified INFβ, compositions containing such modified INFβ proteins or fragments of modified INFβ proteins and related compositions should be considered within the scope of the invention. In another aspect, the present invention relates to nucleic acids encoding modified INFβ entities. In a further aspect the present invention relates to methods for therapeutic treatment of humans using the modified INFβ proteins. In a further aspect still, the invention relates to methods for therapeutic treatment using pharmaceutical preparations comprising peptide or derivative molecules with sequence identity or part identity with the sequences herein disclosed as R1 or R2.

The invention will now be illustrated, but not limited, by the following examples.

Example 1

There are a number of factors that play important roles in determining the total structure of a protein or polypeptide. First, the peptide bond, i.e., that bond which joins the amino acids in the chain together, is a covalent bond. This bond is planar in structure, essentially a substituted amide. An "amide" is any of a group of organic compounds containing the grouping —CONH—.

The planar peptide bond linking Cα of adjacent amino acids may be represented as depicted below:

$$\begin{array}{c} \diagup \\ Cα\text{------}H \\ \diagup\ \ \ \ \ \ \ \diagdown\ \ \diagup \\ \ \ \ \ C=N \\ \diagup\ \ \ \diagdown\ \ \ \diagdown \\ O\text{------}Cα \\ \diagdown \end{array}$$

Because the O=C and the C—N atoms lie in a relatively rigid plane, free rotation does not occur about these axes. Hence, a plane schematically depicted by the interrupted line is sometimes referred to as an "amide" or "peptide plane" plane wherein lie the oxygen (O), carbon (C), nitrogen (N), and hydrogen (H) atoms of the peptide backbone. At opposite corners of this amide plane are located the Cα atoms. Since there is substantially no rotation about the O=C and C—N atoms in the peptide or amide plane, a polypeptide chain thus comprises a series of planar peptide linkages joining the Cα atoms.

A second factor that plays an important role in defining the total structure or conformation of a polypeptide or protein is the angle of rotation of each amide plane about the common Cα linkage. The terms "angle of rotation" and "torsion angle" are hereinafter regarded as equivalent terms. Assuming that the O, C, N, and H atoms remain in the amide plane (which is usually a valid assumption, although there may be some slight deviations from planarity of these atoms for some conformations), these angles of rotation define the N and R polypeptide's backbone conformation, i.e., the structure as it exists between adjacent residues. These two angles are known as φ and ψ. A set of the angles $\Phi_1$, $\psi_1$, where the subscript i represents a particular residue of a polypeptide chain, thus effectively defines the polypeptide secondary structure. The conventions used in defining the φ, ψ angles, i.e., the reference points at which the amide planes form a zero degree angle, and the definition of which angle is φ, and which angle is ψ, for a given polypeptide, are defined in the literature. See, e.g., Ramachandran et al. *Adv. Prot. Chem.* 23:283-437 (1968), at pages 285-94, which pages are incorporated herein by reference.

The present method can be applied to any protein, and is based in part upon the discovery that in humans the primary Pocket 1 anchor position of MHC Class II molecule binding grooves has a well designed specificity for particular amino acid side chains. The specificity of this pocket is determined by the identity of the amino acid at position 86 of the beta chain of the MHC Class II molecule. This site is located at the bottom of Pocket 1 and determines the size of the side chain that can be accommodated by this pocket. Marshall, K. W., *J. Immunol.*, 152:4946-4956 (1994). If this residue is a glycine, then all hydrophobic aliphatic and aromatic amino acids (hydrophobic aliphatics being: valine, leucine, isoleucine, methionine and aromatics being: phenylalanine, tyrosine and tryptophan) can be accommodated in the pocket, a preference being for the aromatic side chains. If this pocket residue is a valine, then the side chain of this amino acid protrudes into the pocket and restricts the size of peptide side chains that can be accommodated such that only hydrophobic aliphatic side chains can be accommodated. Therefore, in an amino acid residue sequence, wherever an amino acid with a hydrophobic aliphatic or aromatic side chain is found, there is the potential for a MHC Class II restricted T-cell epitope to be present. If the side-chain is hydrophobic aliphatic, however, it is approximately twice as likely to be associated with a T-cell epitope than an aromatic side chain (assuming an approximately even distribution of Pocket 1 types throughout the global population).

A computational method embodying the present invention profiles the likelihood of peptide regions to contain T-cell epitopes as follows:

(1) The primary sequence of a peptide segment of predetermined length is scanned, and all hydrophobic aliphatic and aromatic side chains present are identified. (2) The hydrophobic aliphatic side chains are assigned a value greater than that for the aromatic side chains; preferably about twice the value assigned to the aromatic side chains, e.g., a value of 2 for a hydrophobic aliphatic side chain and a value of 1 for an aromatic side chain. (3) The values determined to be present are summed for each overlapping amino acid residue segment (window) of predetermined uniform length within the peptide, and the total value for a particular segment (window) is assigned to a single amino acid residue at an intermediate position of the segment (window), preferably to a residue at about the midpoint of the sampled segment (window). This procedure is repeated for each sampled overlapping amino acid residue segment (window). Thus, each amino acid residue of the peptide is assigned a value that relates to the likelihood of a T-cell epitope being present in that particular segment (window). (4) The values calculated and assigned as described in Step 3, above, can be plotted against the amino acid coordinates of the entire amino acid residue sequence being assessed. (5) All portions of the sequence which have a score of a predetermined value, e.g., a value of 1, are deemed likely to contain a T-cell epitope and can be modified, if desired.

This particular aspect of the present invention provides a general method by which the regions of peptides likely to contain T-cell epitopes can be described. Modifications to the peptide in these regions have the potential to modify the MHC Class II binding characteristics.

According to another aspect of the present invention, T-cell epitopes can be predicted with greater accuracy by the use of a more sophisticated computational method which takes into account the interactions of peptides with models of MHC Class II alleles.

The computational prediction of T-cell epitopes present within a peptide according to this particular aspect contemplates the construction of models of at least 42 MHC Class II alleles based upon the structures of all known MHC Class II molecules and a method for the use of these models in the computational identification of T-cell epitopes, the construction of libraries of peptide backbones for each model in order to allow for the known variability in relative peptide backbone alpha carbon (Cα) positions, the construction of libraries of amino-acid side chain conformations for each backbone dock with each model for each of the 20 amino-acid alternatives at positions critical for the interaction between peptide and MHC Class II molecule, and the use of these libraries of backbones and side-chain conformations in conjunction with a scoring function to select the optimum backbone and side-chain conformation for a particular peptide docked with a particular MHC Class II molecule and the derivation of a binding score from this interaction.

Models of MHC Class II molecules can be derived via homology modeling from a number of similar structures found in the Brookhaven Protein Data Bank ("PDB"). These may be made by the use of semi-automatic homology modeling software (Modeller, Sali A. & Blundell T L., 1993. *J. Mol. Biol.*, 234:779-815) which incorporates a simulated annealing function, in conjunction with the CHARMM® force-field for energy minimisation (available from Molecular Simulations Inc., San Diego, Calif.). Alternative modeling methods can be utilized as well.

The present method differs significantly from other computational methods which use libraries of experimentally derived binding data of each amino-acid alternative at each position in the binding groove for a small set of MHC Class II molecules (Marshall, K. W., et al., *Biomed Pept. Proteins Nucleic Acids,* 1(3):157-162) (1995) or yet other computational methods which use similar experimental binding data in order to define the binding characteristics of particular types of binding pockets within the groove, again using a relatively small subset of MHC Class II molecules, and then 'mixing and matching' pocket types from this pocket library to artificially create further 'virtual' MHC Class II molecules (Sturniolo T., et al., *Nat. Biotech,* 17(6): 555-561 (1999). Both prior methods suffer the major disadvantage that, due to the complexity of the assays and the need to synthesize large numbers of peptide variants, only a small number of MHC Class II molecules can be experimentally scanned. Therefore the first prior method can only make predictions for a small number of MHC Class II molecules. The second prior method also makes the assumption that a pocket lined with similar amino-acids in one molecule will have the same binding characteristics when in the context of a different Class II allele and suffers further disadvantages in that only those MHC Class II molecules can be 'virtually' created which contain pockets contained within the pocket library. Using the modeling approach described herein, the structure of any number and type of MHC Class II molecules can be deduced, therefore alleles can be specifically selected to be representative of the global population. In addition, the number of MHC Class II molecules scanned can be increased by making further models further than having to generate additional data via complex experimentation.

The use of a backbone library allows for variation in the positions of the Cα atoms of the various peptides being scanned when docked with particular MHC Class II molecules. This is again in contrast to the alternative prior computational methods described above which rely on the use of simplified peptide backbones for scanning amino-acid binding in particular pockets. These simplified backbones are not likely to be representative of backbone conformations found in 'real' peptides leading to inaccuracies in prediction of peptide binding. The present backbone library is created by superposing the backbones of all peptides bound to MHC Class II molecules found within the Protein Data Bank and noting the root mean square (RMS) deviation between the Cα atoms of each of the eleven amino-acids located within the binding groove. While this library can be derived from a small number of suitable available mouse and human structures (currently 13), in order to allow for the possibility of even greater variability, the RMS figure for each C"-α position is increased by 50%. The average Cα position of each amino-acid is then determined and a sphere drawn around this point whose radius equals the RMS deviation at that position plus 50%. This sphere represents all allowed Cα positions.

Working from the Cα with the least RMS deviation (that of the amino-acid in Pocket 1 as mentioned above, equivalent to Position 2 of the 11 residues in the binding groove), the sphere is three-dimensionally gridded, and each vertex within the grid is then used as a possible location for a Cα of that amino-acid. The subsequent amide plane, corresponding to the peptide bond to the subsequent amino-acid is grafted onto each of these Cαs and the φ and ψ angles are rotated step-wise at set intervals in order to position the subsequent Cα. If the subsequent Cα falls within the 'sphere of allowed positions' for this Cα than the orientation of the dipeptide is accepted, whereas if it falls outside the sphere then the dipeptide is rejected.

This process is then repeated for each of the subsequent Cα positions, such that the peptide grows from the Pocket 1 Cα 'seed', until all nine subsequent Cαs have been positioned from all possible permutations of the preceding Cαs. The process is then repeated once more for the single Cα preceding pocket 1 to create a library of backbone Cα positions located within the binding groove.

The number of backbones generated is dependent upon several factors: The size of the 'spheres of allowed positions'; the fineness of the gridding of the 'primary sphere' at the Pocket 1 position; the fineness of the step-wise rotation of the Φ and ψ angles used to position subsequent Cαs. Using this process, a large library of backbones can be created. The larger the backbone library, the more likely it will be that the optimum fit will be found for a particular peptide within the binding groove of an MHC Class II molecule. Inasmuch as all backbones will not be suitable for docking with all the models of MHC Class II molecules due to clashes with amino-acids of the binding domains, for each allele a subset of the library is created comprising backbones which can be accommodated by that allele.

The use of the backbone library, in conjunction with the models of MHC Class II molecules creates an exhaustive database consisting of allowed side chain conformations for each amino-acid in each position of the binding groove for each MHC Class II molecule docked with each allowed backbone. This data set is generated using a simple steric overlap function where a MHC Class II molecule is docked with a backbone and an amino-acid side chain is grafted onto the backbone at the desired position. Each of the rotatable bonds of the side chain is rotated step-wise at set intervals and the resultant positions of the atoms dependent upon that bond noted. The interaction of the atom with atoms of side-chains of the binding groove is noted and positions are either accepted or rejected according to the following criteria: The sum total of the overlap of all atoms so far positioned must not exceed a pre-determined value. Thus the stringency of the conformational search is a function of the interval used in the step-wise rotation of the bond and the pre-determined limit for the total overlap. This latter value can be small if it is known that a particular pocket is rigid, however the stringency can be relaxed if the positions of pocket side-chains are known to be relatively flexible. Thus allowances can be made to imitate variations in flexibility within pockets of the binding groove. This conformational search is then repeated for every amino-acid at every position of each backbone when docked with each of the MHC Class II molecules to create the exhaustive database of side-chain conformations.

A suitable mathematical expression is used to estimate the energy of binding between models of MHC Class II molecules in conjunction with peptide ligand conformations which have to be empirically derived by scanning the large database of backbone/side-chain conformations described above. Thus a protein is scanned for potential T-cell epitopes by subjecting each possible peptide of length varying between 9 and 20 amino-acids (although the length is kept constant for each scan) to the following computations: An MHC Class II molecule is selected together with a peptide backbone allowed for that molecule and the side-chains corresponding to the desired peptide sequence are grafted on. Atom identity and interatomic distance data relating to a particular side-chain at a particular position on the backbone are collected for each allowed conformation of that amino-acid (obtained from the database described above). This is repeated for each side-chain along the backbone and peptide scores derived using a scoring function. The best score for that backbone is retained and the process repeated for each allowed backbone for the selected model. The scores from all allowed backbones are compared and the highest score is deemed to be the peptide score for the desired peptide in that MHC Class II model. This process is then repeated for each model with every possible peptide derived from the protein being scanned, and the scores for peptides versus models are displayed.

In the context of the present invention, each ligand presented for the binding affinity calculation is an amino-acid segment selected from a peptide or protein as discussed above. Thus, the ligand is a selected stretch of amino acids about 9 to 20 amino acids in length derived from a peptide, polypeptide or protein of known sequence. The terms "amino acids" and "residues" are hereinafter regarded as equivalent terms.

The ligand, in the form of the consecutive amino acids of the peptide to be examined grafted onto a backbone from the backbone library, is positioned in the binding cleft of an MHC Class II molecule from the MHC Class II molecule model library via the coordinates of the C"-α atoms of the peptide backbone and an allowed conformation for each side-chain is selected from the database of allowed conformations. The relevant atom identities and interatomic distances are also retrieved from this database and used to calculate the peptide binding score. Ligands with a high binding affinity for the MHC Class II binding pocket are flagged as candidates for site-directed mutagenesis. Amino-acid substitutions are made in the flagged ligand (and hence in the protein of interest) which is then retested using the scoring function in order to determine changes which reduce the binding affinity below a predetermined threshold value. These changes can then be incorporated into the protein of interest to remove T-cell epitopes.

Binding between the peptide ligand and the binding groove of MHC Class II molecules involves non-covalent interactions including, but not limited to: hydrogen bonds, electrostatic interactions, hydrophobic (lipophilic) interactions and Van der Waal's interactions. These are included in the peptide scoring function as described in detail below.

It should be understood that a hydrogen bond is a non-covalent bond which can be formed between polar or charged groups and consists of a hydrogen atom shared by two other atoms. The hydrogen of the hydrogen donor has a positive charge where the hydrogen acceptor has a partial negative charge. For the purposes of peptide/protein interactions, hydrogen bond donors may be either nitrogens with hydrogen attached or hydrogens attached to oxygen or nitrogen. Hydrogen bond acceptor atoms may be oxygens not attached to hydrogen, nitrogens with no hydrogens attached and one or two connections, or sulphurs with only one connection. Certain atoms, such as oxygens attached to hydrogens or imine nitrogens (e.g. C═NH) may be both hydrogen acceptors or donors. Hydrogen bond energies range from 3 to 7 Kcal/mol and are much stronger than Van der Waal's bonds, but weaker than covalent bonds. Hydrogen bonds are also highly directional and are at their strongest when the donor atom, hydrogen atom and acceptor atom are co-linear.

Electrostatic bonds are formed between oppositely charged ion pairs and the strength of the interaction is inversely proportional to the square of the distance between the atoms according to Coulomb's law. The optimal distance between ion pairs is about 2.8 Å. In protein/peptide interactions, electrostatic bonds may be formed between arginine, histidine or lysine and aspartate or glutamate. The strength of the bond will depend upon the pKa of the ionizing group and the dielectric constant of the medium although they are approximately similar in strength to hydrogen bonds.

Lipophilic interactions are favorable hydrophobic-hydrophobic contacts that occur between he protein and peptide ligand. Usually, these will occur between hydrophobic amino acid side chains of the peptide buried within the pockets of the binding groove such that they are not exposed to solvent. Exposure of the hydrophobic residues to solvent is highly unfavorable since the surrounding solvent molecules are forced to hydrogen bond with each other forming cage-like clathrate structures. The resultant decrease in entropy is highly unfavorable. Lipophilic atoms may be sulphurs which are neither polar nor hydrogen acceptors and carbon atoms which are not polar.

Van der Waal's bonds are non-specific forces found between atoms which are 3-4 Å apart. They are weaker and less specific than hydrogen and electrostatic bonds. The distribution of electronic charge around an atom changes with time and, at any instant, the charge distribution is not symmetric. This transient asymmetry in electronic charge induces a similar asymmetry in neighboring atoms. The resultant attractive forces between atoms reaches a maximum at the Van der Waal's contact distance but diminishes very rapidly at about 1 Å to about 2 Å. Conversely, as atoms become separated by less than the contact distance, increasingly strong repulsive forces become dominant as the outer electron clouds of the atoms overlap. Although the attractive forces are relatively weak compared to electrostatic and hydrogen bonds (about 0.6 Kcal/mol), the repulsive forces in particular may be very important in determining whether a peptide ligand may bind successfully to a protein.

In one embodiment, the Böhm scoring function (SCORE 1 approach) is used to estimate the binding constant. (Böhm, H. J., *J. Comput. Aided Mol. Des.,* 8(3):243-256 (1994) which is hereby incorporated in its entirety). In another embodiment, the scoring function (SCORE2 approach) is used to estimate the binding affinities as an indicator of a ligand containing a T-cell epitope (Böhm, H. J., *J. Comput. Aided Mol. Des.,* 12(4):309-323 (1998) which is hereby incorporated in its entirety). However, the Böhm scoring functions as described in the above references are used to estimate the binding affinity of a ligand to a protein where it is already known that the ligand successfully binds to the protein and the protein/ligand complex has had its structure solved, the solved structure being present in the Protein Data Bank ("PDB"). Therefore, the scoring function has been developed with the benefit of known positive binding data. In order to allow for discrimination between positive and negative binders, a repulsion term must be added to the equation. In addition, a more satisfactory estimate of binding energy is achieved by computing the lipophilic interactions in a pairwise manner rather than using the area based energy term of the above Böhm functions.

Therefore, in a preferred embodiment, the binding energy is estimated using a modified Böhm scoring function. In the modified Böhm scoring function, the binding energy between protein and ligand ($\Delta G_{bind}$) is estimated considering the following parameters: The reduction of binding energy due to the overall loss of translational and rotational entropy of the ligand ($\Delta G_0$); contributions from ideal hydrogen bonds ($\Delta G_{hb}$) where at least one partner is neutral; contributions from unperturbed ionic interactions ($\Delta G_{ionic}$); lipophilic interactions between lipophilic ligand atoms and lipophilic acceptor atoms ($\Delta G_{lipo}$); the loss of binding energy due to the freezing of internal degrees of freedom in the ligand, i.e., the freedom of rotation about each C—C bond is reduced ($\Delta G_{rot}$);

the energy of the interaction between the protein and ligand ($E_{VdW}$). Consideration of these terms gives equation 1:

$$(\Delta G_{bind}) = (\Delta G_0) + (\Delta G_{hb} \times N_{hb}) + (\Delta G_{ionic} \times N_{ionic}) + (\Delta G_{lipo} \times N_{lipo}) + (\Delta G_{rot} + N_{rot}) + (E_{VdW}).$$

Where N is the number of qualifying interactions for a specific term and, in one embodiment, $\Delta G_0$, $\Delta G_{hb}$, $\Delta G_{ionic}$, $\Delta G_{lipo}$ and $\Delta G_{rot}$ are constants which are given the values: 5.4, −4.7, −4.7, −0.17, and 1.4, respectively.

The term $N_{hb}$ is calculated according to equation 2:

$$N_{hb} = \Sigma_{h\text{-}bonds} f(\Delta R, \Delta \alpha) \times f(N_{neighb}) \times f_{pcs}$$

$f(\Delta R, \Delta \alpha)$ is a penalty function which accounts for large deviations of hydrogen bonds from ideality and is calculated according to equation 3:

$$f(\Delta R, \Delta - \alpha) = f1(\Delta R) \times f2(\Delta \alpha)$$

Where: $f1((R) = 1$ if $(R <= TOL)$ or $= 1 - ((R - TOL)/0.4$ if $(R <= 0.4 + TOL)$ or $= 0$ if $(R > 0.4 + TOL)$ And: $f2(( ) = 1$ if $(( < 30°)$ or $= 1 - (\Delta \alpha - 30)/50$ if $\Delta \alpha <= 80°$ or $= 0$ if $\Delta \alpha > 80°$ TOL is the tolerated deviation in hydrogen bond length=0.25 Å

$\Delta R$ is the deviation of the H—O/N hydrogen bond length from the ideal value=1.9 Å

$\Delta \alpha$ is the deviation of the hydrogen bond angle $\angle_{N/O-H...O/N}$ from its idealized value of 180°

$f(N_{neighb})$ distinguishes between concave and convex parts of a protein surface and therefore assigns greater weight to polar interactions found in pockets rather than those found at the protein surface. This function is calculated according to equation 4 below:

$$f(N_{neighb}) = (N_{neighb}/N_{neighb,0})^\alpha \text{ where } \alpha = 0.5$$

$N_{neighb}$ is the number of non-hydrogen protein atoms that are closer than 5 Å to any given protein atom.

$N_{neighb,0}$ is a constant=25

$f_{pcs}$ is a function which allows for the polar contact surface area per hydrogen bond and therefore distinguishes between strong and weak hydrogen bonds and its value is determined according to the following criteria:

$f_{pcs} = \beta$ when $A_{polar}/N_{HB} < 10 \text{ Å}^2$ or $f_{pcs} = 1$ when $A_{polar}/N_{HB} > 10 \text{ Å}^2$ $A_{polar}$ is the size of the polar protein-ligand contact surface $N_{HB}$ is the number of hydrogen bonds $\beta$ is a constant whose value=1.2

For the implementation of the modified Böhm scoring function, the contributions from ionic interactions, $\Delta G_{ionic}$, are computed in a similar fashion to those from hydrogen bonds described above since the same geometry dependency is assumed.

The term $N_{lipo}$ is calculated according to equation 5 below:

$$N_{lipo} = E_{1L} f(r_{1L})$$

$f(r_{1L})$ is calculated for all lipophilic ligand atoms, l, and all lipophilic protein atoms, L, according to the following criteria:

$$f(r_{1L}) = 1 \text{ when } r_{1L} <= R1 \quad f(r_{1L}) = (r_{1L} - R1)/(R2 - R1) \text{ when } R2 < r_{1L} > R1$$

$$f(r_{1L}) = 0 \text{ when } r_{1L} >= R2$$

Where: $R1 = r_1^{vdw} + r_L^{vdw} + 0.5$ and $R2 = R1 + 3.0$ and $r_1^{vdw}$ is the Van der Waal's radius of atom l and $r_L^{vdw}$ is the Van der Waal's radius of atom L The term $N_{rot}$ is the number of rotable bonds of the amino acid side chain and is taken to be the number of acyclic $sp^3-sp^3$ and $sp^3-sp^2$ bonds. Rotations of terminal —CH$_3$ or —NH$_3$ are not taken into account.

The final term, $E_{VdW}$, is calculated according to equation 6 below:

$$E_{VdW} = \in_1 \in_2 ((r_1^{vdw} + r_2^{vdw})^{12}/r^{12} - (r_1^{vdw} + r_2^{vdw})^6/r^6),$$

where:

$\in_1$ and $\in_2$ are constants dependant upon atom identity $r_1^{vdw} + r_2^{vdw}$ are the Van der Waal's atomic radii r is the distance between a pair of atoms.

With regard to Equation 6, in one embodiment, the constants $\in_1$ and $\in_2$ are given the atom values: C, 0.245; N, 0.283; O, 0.316; S, 0.316, respectively (i.e. for atoms of Carbon, Nitrogen, Oxygen and Sulphur, respectively). With regards to equations 5 and 6, the Van der Waal's radii are given the atom values C, 1.85; N, 1.75; O, 1.60, S, 2.00 Å.

It should be understood that all predetermined values and constants given in the equations above are determined within the constraints of current understandings of protein ligand interactions with particular regard to the type of computation being undertaken herein. Therefore, it is possible that, as this scoring function is refined further, these values and constants may change hence any suitable numerical value which gives the desired results in terms of estimating the binding energy of a protein to a ligand may be used and hence fall within the scope of the present invention.

As described above, the scoring function is applied to data extracted from the database of side-chain conformations, atom identities, and interatomic distances. For the purposes of the present description, the number of MHC Class II molecules included in this database is 42 models plus four solved structures. It should be apparent from the above descriptions that the modular nature of the construction of the computational method of the present invention means that new models can simply be added and scanned with the peptide backbone library and side-chain conformational search function to create additional data sets which can be processed by the peptide scoring function as described above. This allows for the repertoire of scanned MHC Class II molecules to easily be increased, or structures and associated data to be replaced if data are available to create more accurate models of the existing alleles.

The present prediction method can be calibrated against a data set comprising a large number of peptides whose affinity for various MHC Class II molecules has previously been experimentally determined. By comparison of calculated versus experimental data, a cut of value can be determined above which it is known that all experimentally determined T-cell epitopes are correctly predicted.

It should be understood that, although the above scoring function is relatively simple compared to some sophisticated methodologies that are available, the calculations are performed extremely rapidly. It should also be understood that the objective is not to calculate the true binding energy per se for each peptide docked in the binding groove of a selected MHC Class II protein. The underlying objective is to obtain comparative binding energy data as an aid to predicting the location of T-cell epitopes based on the primary structure (i.e. amino acid sequence) of a selected protein. A relatively high binding energy or a binding energy above a selected threshold value would suggest the presence of a T-cell epitope in the ligand. The ligand may then be subjected to at least one round of amino-acid substitution and the binding energy recalculated. Due to the rapid nature of the calculations, these manipulations of the peptide sequence can be performed interactively within the program's user interface on cost-effectively available computer hardware. Major investment in computer hardware is thus not required.

It would be apparent to one skilled in the art that other available software could be used for the same purposes. In particular, more sophisticated software which is capable of docking ligands into protein binding-sites may be used in conjunction with energy minimization. Examples of docking software are: DOCK (Kuntz et al., *J. Mol. Biol.,* 161:269-288 (1982)), LUDI (Böhm, H. J., *J. Comput. Aided Mol. Des.,* 8:623-632 (1994)) and FLEXX (Rarey M., et al., *ISMB,* 3:300-308 (1995)). Examples of molecular modeling and manipulation software include: AMBER® modeling software (Tripos) and CHARMM® modeling software (Molecular Simulations Inc.). The use of these computational methods would severely limit the throughput of the method of this invention due to the lengths of processing time required to make the necessary calculations. However, it is feasible that such methods could be used as a 'secondary screen' to obtain more accurate calculations of binding energy for peptides which are found to be 'positive binders' via the method of the present invention.

The limitation of processing time for sophisticated molecular mechanic or molecular dynamic calculations is one which is defined both by the design of the software which makes these calculations and the current technology limitations of computer hardware. It may be anticipated that, in the future, with the writing of more efficient code and the continuing increases in speed of computer processors, it may become feasible to make such calculations within a more manageable time-frame.

Further information on energy functions applied to macromolecules and consideration of the various interactions that take place within a folded protein structure can be found in: Brooks, B. R., et al., *J. Comput. Chem.,* 4:187-217 (1983) and further information concerning general protein-ligand interactions can be found in: Dauber-Osguthorpe et al., *Proteins* 4(1):31-47 (1988), which are incorporated herein by reference in their entirety. Useful background information can also be found, for example, in Fasman, G. D., ed., *Prediction of Protein Structure and the Principles of Protein Conformation,* Plenum Press, New York, ISBN: 0-306 4313-9.

Example 2

The interaction between MHC, peptide and T-cell receptor (TCR) provides the structural basis for the antigen specificity of T-cell recognition. T-cell proliferation assays test the binding of peptides to MHC and the recognition of MHC/peptide complexes by the TCR. In vitro T-cell proliferation assays of the present example, involve the stimulation of peripheral blood mononuclear cells (PBMCs), containing antigen presenting cells (APCs) and T-cells. Stimulation is conducted in vitro using synthetic peptide antigens, and in some experiments whole protein antigen. Stimulated T-cell proliferation is measured using $^3$H-thymidine ($^3$H-Thy) and the presence of incorporated $^3$H-Thy assessed using scintillation counting of washed fixed cells.

Buffy coats from human blood stored for less than 12 hours were obtained from the National Blood Service (Addenbrooks Hospital, Cambridge, UK). Ficoll-paque was obtained from Amersham Pharmacia Biotech (Amersham, UK). Serum free AIM V media for the culture of primary human lymphocytes and containing L-glutamine, 50 μg/mL streptomycin, 10 μg/mL gentomycin and 0.1% human serum albumin was from Gibco-BRL (Paisley, UK). Synthetic peptides were obtained from Eurosequence (Groningen, The Netherlands) and Babraham Technix (Cambridge, UK). Erythrocytes and leukocytes were separated from plasma and platelets by gentle centrifugation of buffy coats. The top phase (containing plasma and platelets) was removed and discarded. Erythrocytes and leukocytes were diluted 1:1 in phosphate buffered saline (PBS) before layering onto 15 ml ficoll-paque (Amersham Pharmacia, Amersham UK). Centrifugation was done according to the manufacturers recommended conditions and PBMCs were harvested from the serum+PBS/ficoll paque interface. PBMCs were mixed with PBS (1:1) and collected by centrifugation. The supernatant was removed and discarded and the PBMC pellet resuspended in 50 ml PBS. Cells were again pelleted by centrifugation and the PBS supernatant discarded. Cells were resuspended using 50 ml AIM V media and at this point counted and viability assessed using trypan blue dye exclusion. Cells were again collected by centrifugation and the supernatant discarded. Cells were resuspended for cryogenic storage at a density of $3\times10^7$ per mL. The storage medium was 90% (v/v) heat inactivated AB human serum (Sigma, Poole, UK) and 10% (v/v) DMSO (Sigma, Poole, UK). Cells were transferred to a regulated freezing container (Sigma) and placed at −70° C. overnight. When required for use, cells were thawed rapidly in a water bath at 37° C. before transferring to 10 ml pre-warmed AIM V medium.

PBMC were stimulated with protein and peptide antigens in a 96 well flat bottom plate at a density of $2\times10^5$ PBMC per well. PBMC were incubated for 7 days at 37° C. before pulsing with $^3$H-Thy (Amersham-Phamacia, Amersham, UK). For the present study, synthetic peptides (15mers) that overlapped by 3aa increments were generated that spanned the entire sequence of INFβ. Peptide identification numbers (ID#) and sequences are given in FIG. 5. Each peptide was screened individually against PBMC's isolated from 20 naïve donors. Two control peptides that have previously been shown to be immunogenic and a potent non-recall antigen KLH were used in each donor assay. The control antigens used in this study are shown in Table 1.

TABLE 1

Control Antigens

| Peptide | Sequence |
|---|---|
| C-32 | Biotin-PKYVKQNTLKLAT (SEQ. ID NO: 6)<br>Flu haemagglutinin 307-319 |
| C-49 | KVVDQIKKISKPVQH (SEQ ID NO: 7)<br>Chlamydia HSP 60 peptide |
| KLH | Whole protein from Keyhole Limpet Hemocyanin. |

Peptides were dissolved in DMSO to a final concentration of 10 mM, these stock solutions were then diluted 1/500 in AIM V media (final concentration 20 μM). Peptides were added to a flat bottom 96 well plate to give a final concentration of 2 and 20 μM in a 100 μl. The viability of thawed PBMC's was assessed by trypan blue dye exclusion, cells were then resuspended at a density of $2\times10^6$ cells/mL, and 100 µl ($2\times10^5$ PBMC/well) was transferred to each well containing peptides. Triplicate well cultures were assayed at each peptide concentration. Plates were incubated for 7 days in a humidified atmosphere of 5% $CO_2$ at 37° C. Cells were pulsed for 18-21 hours with 1 µCi $^3$H-Thy/well before harvesting onto filter mats. CPM values were determined using a Wallac microplate beta top plate counter (Perkin Elmer). Results were expressed as stimulation indices, determined using the following formula:

Proliferation to Test Peptide CPM

Proliferation in Untreated Wells CPM

Mapping T cell epitopes in the INFβ sequence using the T cell proliferation assay resulted in the identification of two immunogenic regions R1 and R2. This was determined by T cell proliferation in six donors that responded to peptides in one or more of these regions. Regions 1 and 2 induce T-cell proliferation in certain individuals. The cumulative response data for the responding individuals is depicted in FIG. 6, and data from individual responders given in FIG. 7. The epitope data for INFβ and indicating R1 and R2 and the individual peptide/donor responses is depicted in FIG. 8 and FIG. 9.

Example 3

A number of modified INFβ molecules were made using conventional recombinant DNA techniques. A wild-type INFβ gene was used both as a control reagent, and a template from which to derive modified genes by site-directed mutagenesis. Wild-type and modified genes were inserted into a eukaryotic expression vector and the recombinant INFβ proteins expressed as fusion protein with the human immunoglobulin constant region domain. Recombinant proteins were prepared from transiently transfected human embryonic kidney cells and assayed as detailed in EXAMPLE 4.

In order to obtain expression from human embryonic kidney cells, the wild-type human INFβ gene was obtained from the American Type Culture Collection (ATCC, accession no. 31902) and PCR cloned into vector pd-Cs (Lo, et al. (1998), *Protein Engineering* 11: 495). The pd-Cs vector directs the expression of a fusion protein containing the human immunoglobulin constant region domain. The pd-Cs vector containing the wild-type INFβ gene was termed pdCs INFβWT.

Single or multiple codon mutations to generate modified INFβ genes was conducted by mutagenic PCR using pdCsIFNβWT as a template. Overlap PCR was used to combine the two mutated halves of the interferon sequence. The PCR product of 503 bp was digested with XmaI and BamHI, purified using a QIAGEN® gel extraction kit (QIAGEN, Crawley, UK) and transferred into prepared pd-Cs from which the INFβ sequence had been removed using XmaI and BamHI. A positive clone was selected and the INFβ sequence confirmed by sequence analysis.

Mutagenesis was conducted using flanking primers OL575 and OL576 in separate reactions in combination with specific mutagenic (mis-matched) primers and the pdCs INFβWT template DNA.

```
OL575 (XmaI)
5' CTCCCTGTCCCCGGGTATGAG 3';    (SEQ ID NO: 8)
and

OL576 (XhoI/BamHI)
5'-CTTATCATGTCTGGATCCCTCGAG-3'.  (SEQ ID NO: 9)
```

Reactions were conducted using EXPAND HI FIDELITY™ PCR reagents (Roche,GmbH) and reaction conditions specified by the following cycle:

94° C./2'+25 Cycles@94° C./30",60° C./30",72° C./30"+72° C./10'

The products of the separate reactions were joined by PCR in a reaction driven by primers OL575 and OL576 using 15 cycles of PCR as above.

PCR products were gel purified using commercially available kit systems (QIAGEN® gel extraction kit). The desired clones were digested with BamH1 and Xma1 and the purified product ligated into a prepared pd-Cs vector. Cloning was conducted using *E. coli* XL1-Blue cells (Strategene Europe) and culture conditions recommended by the supplier. Sequence confirmation was conducted on all final vector preparations using OL575 and OL576 as sequencing primers.

Expression of modified INFβ-1a human IgFc fusion proteins was achieved using HEK293 human embryonic kidney cell line as the expression host. All DNA for transfection was prepared using the high purity QIAGEN® midi-prep system and instructions provided by the supplier. DNA is filter sterilised prior to use and quantified by measurement of the $A_{260}$. Concentrations were adjusted to 0.5-1.0 µg/µL.

For transient expression, HEK293 were grown using DMEM L-GLUTAMAX™ medium (Invitrogen, Paisley, UK) supplemented with 10% FBS and 250 µg/mL GENETICIN® antibiotic. Prior to transfection, cells were collected by treatment with trypsin and washed using PBS. After 2 cycles of washing cells are taken into fresh medium at a density of $4\times10^5$ cells/mL, and plated into multi-well dishes pre-treated with poly-1-lysine to ensure good cell adhesion. Typically, $2\times10^5$ cells are added to each well of a 48 well plate and the plates incubated overnight at 37° C./5% $CO_2$.

Prior to transfection, the medium is replaced in each well and the transfection mixes added. Transfection is conducted using the lipofectamine reagent and instructions provided by the supplier (Invitrogen, Paisley, UK). Briefly, transfection mixes are prepared containing lipofectamine, OPTI-MEM® modified Eagle's medium (Invitrogen, Paisley, UK) and 0.8 µg DNA per well for each expression vector construct. Transfection mixes are added to the cells and the cells incubated for 4-6 hours. The medium is replaced with 0.5 mL fresh media and the cells incubated at 37° C./5% $CO_2$. Samples were taken after 48 hours for analysis by both anti-Fc ELISA and Daudi cell proliferation assay. The media was harvested after 7 days and stored at 4° C. for further analysis as above.

The medium is assayed for the presence of INFβ using an ELISA detecting the human immunglobulin constant region domain of the INFβ-fusion protein. For this assay a mouse anti-human IgG Fc preparation (Sigma, Poole, UK) is used as a capture reagent. The INFβ-HuFc fusion is quantitated with reference to a standard curve generated using a dilution series of a reference human IgG preparation (Sigma). Bound INFβ-Fc fusion or the reference protein is detected using an anti-human IgG peroxidase conjugate (Sigma) and Sigma OPD colourimetric substrate.

Following estimation of the amount of INFβ in the HEK.293 conditioned medium, the conditioned medium is used directly to test the functional activity of the modified INFβ using the anti-proliferation assay as detailed in EXAMPLE 4.

Example 4

Modified interferon molecules of the present invention were tested for their ability to inhibit the growth of human B cell lymphoma line Daudi. The method is broadly as described previously (Mark, D. F. et al. (1984) *Proc. Natl. Acad. Sci. USA* 81: 5662-5666) and involves incubation of Daudi cells with the test interferon. The anti-proliferative effect of the test molecule is measured using a soluble dye substance that undergoes a colour change in the presence of proliferating cells. The induced colour change is measured in a spectrophotometer and any anti-proliferation effect is computed with reference to the colour change recorded in non-treated control cells and cells treated with a standard interferon preparation.

Briefly, Daudi cells (ATCC # CCL-213) were cultured RPMI 1640 Media supplemented with 100 units/mL Penicillin/100 µg/mL Streptomycin and 2 mM L-Glutamine and 20% Fetal Bovine Serum (FBS). All media and supplements were from Gibco (Paisley, UK). The day before assay, cells are replaced into fresh medium at a density $0.9 \times 10^6$/mL and next day replaced into fresh medium as above except containing 10% (v/v) FBS. The cell density is adjusted to be $2 \times 10^5$ cells/mL.

The test and control interferon preparations are diluted into RPMI containing 10% FBS. Dilutions are made into 96-well flat bottom plates to contain 100 ul/well and all samples are set up in triplicate. Typically doubling dilution series are set out across each plate. Positive control wells are also included in triplicate with a starting concentration of the interferon standard (R&D Systems, Abingdon, UK) at 20000 pg/mL. Control wells containing 100 ul media alone (no interferon) are also included. 100 ul of the cells are added to each well, and the plates incubated for 72 hours at 37° C., 5% $CO_2$.

Proliferation is assessed using AQUEOUS ONE™ reagent system and the suppliers recommended protocol (Promega, Southampton, UK). Briefly, 40 µL of the AQUEOUS ONE™ reagent is added to all wells and the substrate mixed. Plates are incubated at 37° C. for one hour, and then transferred to the plate reading instrument for determination of the light absorbance. Readings are taken at 490 nm. Average absorbance at 490 nm is plotted on the Y axis versus concentrations of interferon standard added along the X axis. Interferon concentration is determined using an ELISA technique as detailed in EXAMPLE 3. For each mutant, the INFβ-1a concentration required to achieve 50% inhibition of cell growth ($EC_{50}$) was determined from the plot of absorbance versus concentration.

Results of such an analysis according to the above method for a number of modified INFβ-1a molecules are depicted in FIG. 10. The results indicate retained anti-proliferative properties in the presence of amino acid substitutions within the INFβ sequence.

We claim:

1. A modified human interferon beta (INFβ) which is less immunogenic than human INFβ (SEQ ID NO: 1) when administered in vivo to a human; wherein the modified human INFβ comprises an amino acid residue sequence that differs from SEQ ID NO: 1 by an amino acid residue substitution selected from the group consisting of L57A, L57C, L57D L57E, L57G, L57H, L57K, L57N, L57P, L57Q, L57R, L57S, and L57T and an additional substitution selected from the group consisting of the H140A, H140C, H140G, and H140P.

2. The modified human INFβ of claim 1 comprising the substitution L57A.

3. The modified human INFβ of claim 1 comprising the substitution H140A.

4. The modified human INFβ of claim 1 comprising the substitution L57A and H140A.

5. The modified human INFβ of claim 1 further comprising an additional substitution in SEQ ID NO: 1 selected from the group consisting of C17D, C17E, C17H, C17K, C17N, C17P, C17Q, C17R, C17S, and C17T.

6. The modified human INFβ of claim 5 comprising the substitution C17S.

7. The modified human INFβ of claim 6 comprising the substitution L57A and H140A.

* * * * *

SEQUENCE LISTING

```
<160> NUMB

```
<211> LENGTH: 24
<212> TYPE: PRT
<213> ORGANISM: Artificial Sequence
<220> FEATURE:
<223> OTHER INFORMATION: MHC class II binding epitope

<400> SEQUENCE: 2

Gln Phe Gln Lys Glu Asp Ala Ala Leu Thr Ile Tyr Glu Met Leu Gln
1               5                   10                  15

Asn Ile Phe Ala Ile Phe Arg Gln
            20

<210> SEQ ID NO 3
<211> LENGTH: 21
<212> TYPE: PRT
<213> ORGANISM: Artificial Sequence
<220> FEATURE:
<223> OTHER INFORMATION: MHC class II binding epitope

<400> SEQUENCE: 3

Arg Tyr Tyr Gly Arg Ile Leu His Tyr Leu Lys Ala Lys Glu Tyr Ser
1               5                   10                  15

His Cys Ala Trp Th

```
Lys Asp Arg Met Asn Phe Asp Ile Pro Glu Glu Ile Lys Gln Leu Gln
 35                  40                  45

Gln Xaa Gln Lys Glu Asp Ala Ala Xaa Thr Xaa Xaa Glu Xaa Xaa Gln
 50                  55                  60

Asn Xaa Xaa Ala Xaa Xaa Arg Gln Asp Ser Ser Thr Gly Trp Asn
 65                  70                  75                  80

Glu Thr Ile Val Glu Asn Leu Leu Ala Asn Val Tyr His Gln Ile Asn
 85                  90                  95

His Leu Lys Thr Val Leu Glu Glu Lys Leu Glu Lys Glu Asp Phe Thr
100                 105                 110

Arg Gly Lys Leu Met Ser Ser Leu His Leu Lys Arg Tyr Tyr Gly Arg
115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
165

<210> SEQ ID NO 5
<211> LENGTH: 166
<212> TYPE: PRT
<213> ORGANISM: Artificial Sequence
<220> FEATURE:
<223> OTHER INFORMATION: Human interferon variants
<221> NAME/KEY: VARIANT
<222> LOCATION: 17
<223> OTHER INFORMATION: Xaa = Cys, Ser
<221> NAME/KEY: VARIANT
<222> LOCATION: 125
<223> OTHER INFORMATION: Xaa = Tyr, Ala
<221> NAME/KEY: VARIANT
<222> LOCATION: 126
<223> OTHER INFORMATION: Xaa = Try, Ala
<221> NAME/KEY: VARIANT
<222> LOCATION: 129
<223> OTHER INFORMATION: Xaa = Ile, Ala
<221> NAME/KEY: VARIANT
<222> LOCATION: 130
<223> OTHER INFORMATION: Xaa = Leu, Ala
<221> NAME/KEY: VARIANT
<222> LOCATION: (132)...(132)
<223> OTHER INFORMATION: Xaa = Tyr, Ser
<221> NAME/KEY: VARIANT
<222> LOCATION: (133)...(133)
<223> OTHER INFORMATION: Xaa = Leu, Ala
<221> NAME/KEY: VARIANT
<222> LOCATION: (138)...(138)
<223> OTHER INFORMATION: Xaa = Tyr, His, Ala

<400> SEQUENCE: 5

Met Ser Tyr Asn Leu Leu Gly Phe Leu Gln Arg Ser Ser Asn Phe Gln
  1               5                  10                  15

Xaa Gln Lys Leu Leu Trp Gln Leu Asn Gly Arg Leu Glu Tyr Cys Leu
 20                  25                  30

Lys Asp Arg Met Asn Phe Asp Ile Pro Glu Glu Ile Lys Gln Leu Gln
 35                  40                  45

Gln Phe Gln Lys Glu Asp Ala Ala Leu Thr Ile Tyr Glu Met Leu Gln
 50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
 85                  90                  95
```

His Leu Lys Thr Val Leu Glu Glu Lys Leu Glu Lys Glu Asp Phe Thr
100                 105                 110

Arg Gly Lys Leu Met Ser Ser Leu His Leu Lys Arg Xaa Xaa Gly Arg
115                 120                 125

Xaa Xaa His Xaa Xaa Lys Ala Lys Glu Xaa Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
165

<210> SEQ ID NO 6
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 6

Pro Lys Tyr Val Lys Gln Asn Thr Leu Lys Leu Ala Thr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 7

Lys Val Val Asp Gln Ile Lys Lys Ile Ser Lys Pro Val Gln His
1               5                   10                  15

<210> SEQ ID NO 8
<211> LENGTH: 21
<212> TYPE: PRT
<213> ORGANISM: Artificial Sequence
<220> FEATURE:
<223> OTHER INFORMATION: MHC class II binding epitope

<400> SEQUENCE: 8

Cys Thr Cys Cys Cys Thr Gly Thr Cys Cys Cys Cys Gly Gly Gly Thr
1               5                   10                  15

Ala Thr Gly Ala Gly
20

<210> SEQ ID NO 9
<211> LENGTH: 24
<212> TYPE: PRT
<213> ORGANISM: Artificial Sequence
<220> FEATURE:
<223> OTHER INFORMATION: MHC class II binding epitope

<400> SEQUENCE: 9

Cys Thr Thr Ala Thr Cys Ala Thr Gly Thr Cys Thr Gly Gly Ala Thr
1               5                   10                  15

Cys Cys Cys Thr Cys Gly Ala Gly
20

<210> SEQ ID NO 10
<211> LENGTH: 13
<212> TYPE: PRT
<213> ORGANISM: Artificial Sequence
<220> FEATURE:

```
<223> OTHER INFORMATION: MHC class II binding epitope

<400> SEQUENCE: 10

Met Ser Tyr Asn Leu Leu Gly Phe Leu Gln Arg Ser Ser
1               5                   10

<210> SEQ ID NO 11
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 11

Tyr Asn Leu Leu Gly Phe Leu Gln Arg Ser Ser Asn Phe
1               5                   10

<210> SEQ ID NO 12
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 12

Asn Leu Leu Gly Phe Leu Gln Arg Ser Ser Asn Phe Gln
1               5                   10

<210> SEQ ID NO 13
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 13

Leu Leu Gly Phe Leu Gln Arg Ser Ser Asn Phe Gln Cys
1               5                   10

<210> SEQ ID NO 14
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 14

Leu Gly Phe Leu Gln Arg Ser Ser Asn Phe Gln Cys Gln
1               5                   10

<210> SEQ ID NO 15
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 15

Gly Phe Leu Gln Arg Ser Ser Asn Phe Gln Cys Gln Lys
1               5                   10

<210> SEQ ID NO 16
<211> LENGTH: 13
<212> TYPE: PRT
<213> ORGANISM: Artificial Sequence
<220> FEATURE:
<223> OTHER INFORMATION: MHC class II binding epitope
```

-continued

<400> SEQUENCE: 16

Arg Ser Ser Asn Phe Gln Cys Gln Lys Leu Leu Trp Gln
1               5                   10

<210> SEQ ID NO 17
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 17

Ser Asn Phe Gln Cys Gln Lys Leu Leu Trp Gln Leu Asn
1               5                   10

<210> SEQ ID NO 18
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 18

Gln Lys Leu Leu Trp Gln Leu Asn Gly Arg Leu Glu Tyr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 19

Lys Leu Leu Trp Gln Leu Asn Gly Arg Leu Glu Tyr Cys
1               5                   10

<210> SEQ ID NO 20
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 20

Leu Leu Trp Gln Leu Asn Gly Arg Leu Glu Tyr Cys Leu
1               5                   10

<210> SEQ ID NO 21
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 21

Trp Gln Leu Asn Gly Arg Leu Glu Tyr Cys Leu Lys Asp
1               5                   10

<210> SEQ ID NO 22
<211> LENGTH: 13
<212> TYPE: PRT
<213> ORGANISM: Artificial Sequence
<220> FEATURE:
<223> OTHER INFORMATION: MHC class II binding epitope -continued

```
<400> SEQUENCE: 22

Gly Arg Leu Glu Tyr Cys Leu Lys Asp Arg Met Asn Phe
1               5                   10

<210> SEQ ID NO 23
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 23

Leu Glu Tyr Cys Leu Lys Asp Arg Met Asn Phe Asp Ile
1               5                   10

<210> SEQ ID NO 24
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 24

Tyr Cys Leu Lys Asp Arg Met Asn Phe Asp Ile Pro Glu
1               5                   10

<210> SEQ ID NO 25
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 25

Asp Arg Met Asn Phe Asp Ile Pro Glu Glu Ile Lys Gln
1               5                   10

<210> SEQ ID NO 26
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 26

Met Asn Phe Asp Ile Pro Glu Glu Ile Lys Gln Leu Gln
1               5                   10

<210> SEQ ID NO 27
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 27

Phe Asp Ile Pro Glu Glu Ile Lys Gln Leu Gln Gln Phe
1               5                   10

<210> SEQ ID NO 28
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 28
```

```
Asp Ile Pro Glu Glu Ile Lys Gln Leu Gln Gln Phe Gln
1               5                   10
```

<210> SEQ ID NO 29
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 29

```
Glu Glu Ile Lys Gln Leu Gln Gln Phe Gln Lys Glu Asp
1               5                   10
```

<210> SEQ ID NO 30
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 30

```
Lys Gln Leu Gln Gln Phe Gln Lys Glu Asp Ala Ala Leu
1               5                   10
```

<210> SEQ ID NO 31
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 31

```
Gln Leu Gln Gln Phe Gln Lys Glu Asp Ala Ala Leu Thr
1               5                   10
```

<210> SEQ ID NO 32
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 32

```
Gln Gln Phe Gln Lys Glu Asp Ala Ala Leu Thr Ile Tyr
1               5                   10
```

<210> SEQ ID NO 33
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 33

```
Phe Gln Lys Glu Asp Ala Ala Leu Thr Ile Tyr Glu Met
1               5                   10
```

<210> SEQ ID NO 34
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 34

```
Lys Glu Asp Ala Ala Leu Thr Ile Tyr Glu Met Leu Gln
1               5                   10

<210> SEQ ID NO 35
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 35

Ala Ala Leu Thr Ile Tyr Glu Met Leu Gln Asn Ile Phe
1               5                   10

<210> SEQ ID NO 36
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 36

Leu Thr Ile Tyr Glu Met Leu Gln Asn Ile Phe Ala Ile
1               5                   10

<210> SEQ ID NO 37
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 37

Thr Ile Tyr Glu Met Leu Gln Asn Ile Phe Ala Ile Phe
1               5                   10

<210> SEQ ID NO 38
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 38

Ile Tyr Glu Met Leu Gln Asn Ile Phe Ala Ile Phe Arg
1               5                   10

<210> SEQ ID NO 39
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 39

Tyr Glu Met Leu Gln Asn Ile Phe Ala Ile Phe Arg Gln
1               5                   10

<210> SEQ ID NO 40
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 40

Glu Met Leu Gln Asn Ile Phe Ala Ile Phe Arg Gln Asp
```

```
<210> SEQ ID NO 41
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 41

Gln Asn Ile Phe Ala Ile Phe Arg Gln Asp Ser Ser Ser
1               5                   10

<210> SEQ ID NO 42
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 42

Asn Ile Phe Ala Ile Phe Arg Gln Asp Ser Ser Ser Thr
1               5                   10

<210> SEQ ID NO 43
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 43

Phe Ala Ile Phe Arg Gln Asp Ser Ser Ser Thr Gly Trp
1               5                   10

<210> SEQ ID NO 44
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 44

Ala Ile Phe Arg Gln Asp Ser Ser Ser Thr Gly Trp Asn
1               5                   10

<210> SEQ ID NO 45
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 45

Thr Gly Trp Asn Glu Thr Ile Val Glu Asn Leu Leu Ala
1               5                   10

<210> SEQ ID NO 46
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 46

Gly Trp Asn Glu Thr Ile Val Glu Asn Leu Leu Ala Asn
1               5                   10
```

```
<210> SEQ ID NO 47
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 47

Trp Asn Glu Thr Ile Val Glu Asn Leu Leu Ala Asn Val
1               5                   10

<210> SEQ ID NO 48
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 48

Glu Thr Ile Val Glu Asn Leu Leu Ala Asn Val Tyr His
1               5                   10

<210> SEQ ID NO 49
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 49

Thr Ile Val Glu Asn Leu Leu Ala Asn Val Tyr His Gln
1               5                   10

<210> SEQ ID NO 50
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 50

Glu Asn Leu Leu Ala Asn Val Tyr His Gln Ile Asn His
1               5                   10

<210> SEQ ID NO 51
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 51

Asn Leu Leu Ala Asn Val Tyr His Gln Ile Asn His Leu
1               5                   10

<210> SEQ ID NO 52
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 52

Ala Asn Val Tyr His Gln Ile Asn His Leu Lys Thr Val
1               5                   10
```

```
<210> SEQ ID NO 53
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 53

Asn Val Tyr His Gln Ile Asn His Leu Lys Thr Val Leu
1               5                   10

<210> SEQ ID NO 54
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 54

His Gln Ile Asn His Leu Lys Thr Val Leu Glu Glu Lys
1               5                   10

<210> SEQ ID NO 55
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 55

Asn His Leu Lys Thr Val Leu Glu Glu Lys Leu Glu Lys
1               5                   10

<210> SEQ ID NO 56
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 56

Lys Thr Val Leu Glu Glu Lys Leu Glu Lys Glu Asp Phe
1               5                   10

<210> SEQ ID NO 57
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 57

Thr Val Leu Glu Glu Lys Leu Glu Lys Glu Asp Phe Thr
1               5                   10

<210> SEQ ID NO 58
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 58

Val Leu Glu Glu Lys Leu Glu Lys Glu Asp Phe Thr Arg
1               5                   10
```

```
<210> SEQ ID NO 59
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 59

Glu Lys Leu Glu Lys Glu Asp Phe Thr Arg Gly Lys Leu
1               5                   10

<210> SEQ ID NO 60
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 60

Lys Leu Glu Lys Glu Asp Phe Thr Arg Gly Lys Leu Met
1               5                   10

<210> SEQ ID NO 61
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 61

Leu Glu Lys Glu Asp Phe Thr Arg Gly Lys Leu Met Ser
1               5                   10

<210> SEQ ID NO 62
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 62

Glu Lys Glu Asp Phe Thr Arg Gly Lys Leu Met Ser Ser
1               5                   10

<210> SEQ ID NO 63
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 63

Glu Asp Phe Thr Arg Gly Lys Leu Met Ser Ser Leu His
1               5                   10

<210> SEQ ID NO 64
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 64

Thr Arg Gly Lys Leu Met Ser Ser Leu His Leu Lys Arg
1               5                   10

<210> SEQ ID NO 65
```

```
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 65

Gly Lys Leu Met Ser Ser Leu His Leu Lys Arg Tyr Tyr
1               5                   10

<210> SEQ ID NO 66
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 66

Lys Leu Met Ser Ser Leu His Leu Lys Arg Tyr Tyr Gly
1               5                   10

<210> SEQ ID NO 67
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 67

Leu Met Ser Ser Leu His Leu Lys Arg Tyr Tyr Gly Arg
1               5                   10

<210> SEQ ID NO 68
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 68

Ser Ser Leu His Leu Lys Arg Tyr Tyr Gly Arg Ile Leu
1               5                   10

<210> SEQ ID NO 69
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 69

Leu His Leu Lys Arg Tyr Tyr Gly Arg Ile Leu His Tyr
1               5                   10

<210> SEQ ID NO 70
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 70

Lys Arg Tyr Tyr Gly Arg Ile Leu His Tyr Leu Lys Ala
1               5                   10

<210> SEQ ID NO 71
<211> LENGTH: 13
```

```
<212> TYPE: PRT
<213> ORGANISM: Artificial Sequence
<220> FEATURE:
<223> OTHER INFORMATION: MHC class II binding epitope

<400> SEQUENCE: 71

Arg Tyr Tyr Gly Arg Ile Leu His Tyr Leu Lys Ala Lys
1               5                   10

<210> SEQ ID NO 72
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 72

Tyr Tyr Gly Arg Ile Leu His Tyr Leu Lys Ala Lys Glu
1               5                   10

<210> SEQ ID NO 73
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 73

Gly Arg Ile Leu His Tyr Leu Lys Ala Lys Glu Tyr Ser
1               5                   10

<210> SEQ ID NO 74
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 74

Arg Ile Leu His Tyr Leu Lys Ala Lys Glu Tyr Ser His
1               5                   10

<210> SEQ ID NO 75
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 75

Leu His Tyr Leu Lys Ala Lys Glu Tyr Ser His Cys Ala
1               5                   10

<210> SEQ ID NO 76
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 76

His Tyr Leu Lys Ala Lys Glu Tyr Ser His Cys Ala Trp
1               5                   10

<210> SEQ ID NO 77
<211> LENGTH: 13
<212> TYPE: PRT
```

```
<213> ORGANISM: Artificial Sequence
<220> FEATURE:
<223> OTHER INFORMATION: MHC class II binding epitope

<400> SEQUENCE: 77

Tyr Leu Lys Ala Lys Glu Tyr Ser His Cys Ala Trp Thr
1               5                   10

<210> SEQ ID NO 78
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 78

Lys Glu Tyr Ser His Cys Ala Trp Thr Ile Val Arg Val
1               5                   10

<210> SEQ ID NO 79
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 79

His Cys Ala Trp Thr Ile Val Arg Val Glu Ile Leu Arg
1               5                   10

<210> SEQ ID NO 80
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 80

Cys Ala Trp Thr Ile Val Arg Val Glu Ile Leu Arg Asn
1               5                   10

<210> SEQ ID NO 81
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 81

Trp Thr Ile Val Arg Val Glu Ile Leu Arg Asn Phe Tyr
1               5                   10

<210> SEQ ID NO 82
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 82

Thr Ile Val Arg Val Glu Ile Leu Arg Asn Phe Tyr Phe
1               5                   10

<210> SEQ ID NO 83
<211> LENGTH: 13
<212> TYPE: PRT
<213> ORGANISM: Artificial Sequence
```

```
<220> FEATURE:
<223> OTHER INFORMATION: MHC class II binding epitope

<400> SEQUENCE: 83

Ile Val Arg Val Glu Ile Leu Arg Asn Phe Tyr Phe Ile
1               5                   10

<210> SEQ ID NO 84
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 84

Val Arg Val Glu Ile Leu Arg Asn Phe Tyr Phe Ile Asn
1               5                   10

<210> SEQ ID NO 85
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 85

Val Glu Ile Leu Arg Asn Phe Tyr Phe Ile Asn Arg Leu
1               5                   10

<210> SEQ ID NO 86
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 86

Glu Ile Leu Arg Asn Phe Tyr Phe Ile Asn Arg Leu Thr
1               5                   10

<210> SEQ ID NO 87
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 87

Leu Arg Asn Phe Tyr Phe Ile Asn Arg Leu Thr Gly Tyr
1               5                   10

<210> SEQ ID NO 88
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 88

Arg Asn Phe Tyr Phe Ile Asn Arg Leu Thr Gly Tyr Leu
1               5                   10

<210> SEQ ID NO 89
<211> LENGTH: 13
<212> TYPE: PRT
<213> ORGANISM: Artificial Sequence
<220> FEATURE:
```

```
<223> OTHER INFORMATION: MHC class II binding epitope

<400> SEQUENCE: 89

Asn Phe Tyr Phe Ile Asn Arg Leu Thr Gly Tyr Leu Arg
1               5                   10

<210> SEQ ID NO 90
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 90

Phe Tyr Phe Ile Asn Arg Leu Thr Gly Tyr Leu Arg Asn
1               5                   10

<210> SEQ ID NO 91
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 91

Met Ser Tyr Asn Leu Leu Gly Phe Leu Gln Arg Ser Ser Asn Phe
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 92

Asn Leu Leu Gly Phe Leu Gln Arg Ser Ser Asn Phe Gln Cys Gln
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 93

Gly Phe Leu Gln Arg Ser Ser Asn Phe Gln Cys Gln Lys Leu Leu
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 94

Gln Arg Ser Ser Asn Phe Gln Cys Gln Lys Leu Leu Trp Gln Leu
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: MHC class II binding epitope
```

<400> SEQUENCE: 95

Ser Asn Phe Gln Cys Gln Lys Leu Leu Trp Gln Leu Asn Gly Arg
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 96

Gln Cys Gln Lys Leu Leu Trp Gln Leu Asn Gly Arg Leu Glu Tyr
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 97

Lys Leu Leu Trp Gln Leu Asn Gly Arg Leu Glu Tyr Cys Leu Lys
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 98

Trp Gln Leu Asn Gly Arg Leu Glu Tyr Cys Leu Lys Asp Arg Met
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 99

Asn Gly Arg Leu Glu Tyr Cys Leu Lys Asp Arg Met Asn Phe Asp
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 100

Leu Glu Tyr Cys Leu Lys Asp Arg Met Asn Phe Asp Ile Pro Glu
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: MHC class II binding epitope

```
<400> SEQUENCE: 101

Cys Leu Lys Asp Arg Met Asn Phe Asp Ile Pro Glu Glu Ile Lys
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 102

Asp Arg Met Asn Phe Asp Ile Pro Glu Glu Ile Lys Gln Leu Gln
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 103

Asn Phe Asp Ile Pro Glu Glu Ile Lys Gln Leu Gln Gln Phe Gln
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 104

Ile Pro Glu Glu Ile Lys Gln Leu Gln Gln Phe Gln Lys Glu Asp
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 105

Glu Ile Lys Gln Leu Gln Gln Phe Gln Lys Glu Asp Ala Ala Leu
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 106

Gln Leu Gln Gln Phe Gln Lys Glu Asp Ala Ala Leu Thr Ile Tyr
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 107
```

```
Gln Phe Gln Lys Glu Asp Ala Ala Leu Thr Ile Tyr Glu Met Leu
1               5                   10                  15
```

<210> SEQ ID NO 108
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 108

```
Lys Glu Asp Ala Ala Leu Thr Ile Tyr Glu Met Leu Gln Asn Ile
1               5                   10                  15
```

<210> SEQ ID NO 109
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 109

```
Ala Ala Leu Thr Ile Tyr Glu Met Leu Gln Asn Ile Phe Ala Ile
1               5                   10                  15
```

<210> SEQ ID NO 110
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 110

```
Thr Ile Tyr Glu Met Leu Gln Asn Ile Phe Ala Ile Phe Arg Gln
1               5                   10                  15
```

<210> SEQ ID NO 111
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 111

```
Glu Met Leu Gln Asn Ile Phe Ala Ile Phe Arg Gln Asp Ser Ser
1               5                   10                  15
```

<210> SEQ ID NO 112
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 112

```
Gln Asn Ile Phe Ala Ile Phe Arg Gln Asp Ser Ser Ser Thr Gly
1               5                   10                  15
```

<210> SEQ ID NO 113
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 113

Phe Ala Ile Phe Arg Gln Asp Ser Ser Ser Thr Gly Trp Asn Glu
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 114

Phe Arg Gln Asp Ser Ser Ser Thr Gly Trp Asn Glu Thr Ile Val
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 115

Asp Ser Ser Ser Thr Gly Trp Asn Glu Thr Ile Val Glu Asn Leu
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 116

Ser Thr Gly Trp Asn Glu Thr Ile Val Glu Asn Leu Leu Ala Asn
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 117

Trp Asn Glu Thr Ile Val Glu Asn Leu Leu Ala Asn Val Tyr His
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 118

Thr Ile Val Glu Asn Leu Leu Ala Asn Val Tyr His Gln Ile Asn
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 119

Glu Asn Leu Leu Ala Asn Val Tyr His Gln Ile Asn His Leu Lys

```
<210> SEQ ID NO 120
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 120

Leu Ala Asn Val Tyr His Gln Ile Asn His Leu Lys Thr Val Leu
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 121

Val Tyr His Gln Ile Asn His Leu Lys Thr Val Leu Glu Glu Lys
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 122

Gln Ile Asn His Leu Lys Thr Val Leu Glu Glu Lys Leu Glu Lys
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 123

His Leu Lys Thr Val Leu Glu Glu Lys Leu Glu Lys Glu Asp Phe
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 124

Thr Val Leu Glu Glu Lys Leu Glu Lys Glu Asp Phe Thr Arg Gly
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 125

Glu Glu Lys Leu Glu Lys Glu Asp Phe Thr Arg Gly Lys Leu Met
1               5                   10                  15
```

-continued

<210> SEQ ID NO 126
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 126

Leu Glu Lys Glu Asp Phe Thr Arg Gly Lys Leu Met Ser Ser Leu
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 127

Glu Asp Phe Thr Arg Gly Lys Leu Met Ser Ser Leu His Leu Lys
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 128

Thr Arg Gly Lys Leu Met Ser Ser Leu His Leu Lys Arg Tyr Tyr
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 129

Lys Leu Met Ser Ser Leu His Leu Lys Arg Tyr Tyr Gly Arg Ile
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 130

Ser Ser Leu His Leu Lys Arg Tyr Tyr Gly Arg Ile Leu His Tyr
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 131

His Leu Lys Arg Tyr Tyr Gly Arg Ile Leu His Tyr Leu Lys Ala
1               5                   10                  15

```
<210> SEQ ID NO 132
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 132

Arg Tyr Tyr Gly Arg Ile Leu His Tyr Leu Lys Ala Lys Glu Tyr
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 133

Gly Arg Ile Leu His Tyr Leu Lys Ala Lys Glu Tyr Ser His Cys
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 134

Leu His Tyr Leu Lys Ala Lys Glu Tyr Ser His Cys Ala Trp Thr
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 135

Leu Lys Ala Lys Glu Tyr Ser His Cys Ala Trp Thr Ile Val Arg
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 136

Lys Glu Tyr Ser His Cys Ala Trp Thr Ile Val Arg Val Glu Ile
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 137

Ser His Cys Ala Trp Thr Ile Val Arg Val Glu Ile Leu Arg Asn
1               5                   10                  15
```

-continued

```
<210> SEQ ID NO 138
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 138

Ala Trp Thr Ile Val Arg Val Glu Ile Leu Arg Asn Phe Tyr Phe
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 139

Ile Val Arg Val Glu Ile Leu Arg Asn Phe Tyr Phe Ile Asn Arg
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 140

Val Glu Ile Leu Arg Asn Phe Tyr Phe Ile Asn Arg Leu Thr Gly
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: MHC class II binding epitope

<400> SEQUENCE: 141

Leu Arg Asn Phe Tyr Phe Ile Asn Arg Leu Thr Gly Tyr Leu Arg
1               5                   10                  15
```